US005790710A

United States Patent [19]
Price et al.

[11] Patent Number: 5,790,710
[45] Date of Patent: Aug. 4, 1998

[54] AUTOFOCUS SYSTEM FOR SCANNING MICROSCOPY

[75] Inventors: Jeffrey H. Price, 8568 Villa La Jolla Dr. #290, La Jolla, Calif. 92037; David A. Gough, Cardiff, Calif.

[73] Assignee: Jeffrey H. Price, La Jolla, Calif.

[21] Appl. No.: 785,614

[22] Filed: Jan. 17, 1997

Related U.S. Application Data

[63] Continuation of Ser. No. 270,017, Jul. 1, 1994, abandoned, which is a continuation-in-part of Ser. No. 17,321, Feb. 11, 1993, abandoned, which is a continuation of Ser. No. 729,383, Jul. 12, 1991, abandoned.

[51] Int. Cl.$^6$ .............................. G06K 9/40; G06K 9/00
[52] U.S. Cl. ...................... 382/255; 250/201.3; 348/345; 382/141
[58] Field of Search .................... 382/128, 129, 382/255, 280; 364/413

[56] References Cited

U.S. PATENT DOCUMENTS

| | | | |
|---|---|---|---|
| 4,342,905 | 8/1982 | Fujii et al. | 250/201 |
| 4,561,104 | 12/1985 | Martin | 382/8 |
| 4,639,587 | 1/1987 | Chadwick et al. | 250/201.3 |
| 4,668,618 | 5/1987 | Thornthwaite | 435/6 |
| 4,700,298 | 10/1987 | Palcic et al. | 364/413.1 |
| 4,741,043 | 4/1988 | Bacus | 382/6 |
| 4,803,352 | 2/1989 | Bierleutgeb | 250/201.3 |
| 4,829,374 | 5/1989 | Miyamoto et al. | 358/93 |
| 4,845,552 | 7/1989 | Jaggi et al. | 382/128 |
| 4,887,892 | 12/1989 | Bacus | 350/523 |
| 4,906,561 | 3/1990 | Thornthwaite | 435/6 |
| 4,933,471 | 6/1990 | Lee | 549/33 |
| 4,945,220 | 7/1990 | Mallory et al. | 250/201.3 |
| 4,998,284 | 3/1991 | Bacus et al. | 382/6 |
| 5,008,185 | 4/1991 | Bacus | 435/7.23 |
| 5,016,283 | 5/1991 | Bacus et al. | 382/6 |
| 5,018,209 | 5/1991 | Bacus | 382/6 |
| 5,040,228 | 8/1991 | Bose et al. | 382/141 |
| 5,122,698 | 6/1992 | Cohen et al. | 250/201.3 |
| 5,193,124 | 3/1993 | Subbarao | 382/255 |
| 5,239,170 | 8/1993 | Hughlett | 250/201 |

FOREIGN PATENT DOCUMENTS

| | | | |
|---|---|---|---|
| 0163394 A2 | 12/1985 | European Pat. Off. | G02B 21/24 |
| 2615841 A1 | 10/1977 | Netherlands | H04N 5/34 |
| 3828381 A1 | 3/1990 | Netherlands | G02B 7/09 |
| 4226523 A1 | 2/1994 | Netherlands | G02B 7/28 |

OTHER PUBLICATIONS

Nickolls et al. "Pre-Processing of Images of an Automated Chromosome Analysis System"–1981 Pattern Recog. Society.

R.I. Freshney, "The Transformed Phenotype", in Culture of Animal Cells, a Manual of Basic Technique, 2nd ed., New York: Alan R. Liss, pp. 197–206, 1987.

C. De Le Torre, et al., "Estimation of Chromatin Patterns at G1, S, and G2 of the Cell Cycle", Exp. Cell Res., vol. 88, pp. 171–174, 1974.

(List continued on next page.)

*Primary Examiner*—Joseph Mancuso
*Assistant Examiner*—Jayanti K. Patel
*Attorney, Agent, or Firm*—Gray Cary Ware Freidenrich, LLP

[57] ABSTRACT

Reliable autofocus is required to obtain accurate measurements of fluorescent stained cellular components from a system capable of scanning multiple microscope fields. Autofocus could be performed directly with fluorescence images, but due to photobleaching and destructive fluorescence by-products, it is best to minimize fluorescence exposure for photosensitive specimens and live cells. This exposure problem could be completely avoided by using phase-contrast microscopy, implemented through the same optics as fluorescence microscopy. Functions for both phase-contrast and fluorescence autofocus were evaluated using the present invention and the suitability of phase-contrast autofocus for fluorescence microscopy was determined. The present autofocus system for scanning microscopy can be performed at least as fast as 0.25 s/field without loss of precision.

20 Claims, 20 Drawing Sheets

OTHER PUBLICATIONS

W. Sawicki, et al., "Change of Chromatin Morphology During the Cell Cycle Detected by Means of Automated Image Analysis", J. Cell Physiol., vol. 84, pp. 423–428, 1974.

F. Giroud, "Cell Nucleus Pattern Analysis: Geometric and Densitometric Featuring, Automatic Cell Phase Identification", Biol. Cell., vol. 44, pp. 177–188, 1982.

E. A. Dawes, Quantitative Problems in Biochemistry, Baltimore: Williams and Wilkins, pp. 293–311, 1972.

R.I. Freshney, Culture of Animal Cells, a Manual of Basic Technique, 2nd ed., New York: Alan R Liss, Chapters 18 and 19, pp. 227–256, 1987.

B. H. Mayall, "Current Capabilities and Clinical Applications of Image Cytometry", Cytometry, Supplement 3, pp. 78–84, 1988.

G. Thurston, et al., "Cell Motility Measurements with an Automated Microscope System", Exp. Cell Res., vol. 165, pp. 380–390, 1986.

E. Colomb, et al., "Cell Cycle Studies by Multiparametric Automatic Scanning of Topographically Preserved Cells in Culture", Cytometry, vol. 10, pp. 263–272, 1989.

C.J. Cornelisse, et al., "DNA Image Cytometry on Machine–Selected Breast Cancer Cells and a Comparison Between Flow Cytometry and Scanning Cytophotometry", Cytometry, vol. 6, pp. 471–477, 1985.

S.S. Roberts, "Unfatal Vision: Image Cytometry Boosts Cancer Diagnosis", J. NIH Research, vol. 2, pp. 77–79, 1990.

C.J. Herman, et al., "Recent Progress in Clinical Quantitative Cytology", Arch. Pathol. Lab. Meth., vol. 111, pp. 505–512, 1987.

J.P.A. Baak, "Quantitative Pathology Today –A Technical View", Path. Res. Pract., vol. 182, pp. 396–400, 1987.

L. O'gorman, et al., "A System for Automated Liver Tissue Image Analysis: Methods and Results", IEEE Transactions on Biomedical Engineering, vol. 32, pp. 696–706, 1985.

T. Takamatsu, et al., "Quantitative Fluorescence Image Analysis", Acta Histochem. Cytochem., vol. 19, pp. 61–71, 1986.

K.S. Fu, et al., "A Survey on Image Segmentation", Pattern Recognition, vol. 13, pp. 3–16, 1981.

C.J. Moran, "A Morphological Transformation for Sharpening Edges of Features before Segmentatioin", Computer Vision, Graphics and Image Processing, vol. 49, pp. 85–94, 1990.

S. Hamada, et al., "DAPI Staining Improved for Quantitative Cytofluorometry", Histochem., vol. 79, pp. 219–226, 1983.

G.L. Wied, eta l., "Image Analysis in Quantitative Cytoopathology and Histopathology", Human Pathology, vol. 20, pp. 549–571, 1989.

N.M. McKenna, et al., "Culturing Cells on the Microscope Stage", in Fluorescence Microscopy of Living Cells in Culture, Part A, Methods in Cell Biology, vol. 29, Y.L. Wang and D. Lansing Taylor eds., San Diego: Academic Press, pp. 195–205, 1989.

R.P. Haugland, Molecular Probes: Handbook of Fluorescent Probes and Research Chemicals, Eugene, Oregon: Molecular Probes, Inc., title page, table of contents, pp. 1–19, 1989.

J.H. Price, Scanning Cytometry for Cell Monolayers, Ph.D. Dissertation, Bioengineering, University of California, San Diego, Nov., 1990.

J.H. Price, et al., "Nuclear Recognition in Images of Fluorescent Stained Cell Monolayers", Presented at the International Society of Optical Engineering (SPIE), Applications of Digital Image Processing XI, Jul. 12, 1990.

K.K. Bose, et al., "Differences in the Flow and Absorption Cytometric DNA Distributions of Mouse Hepatocytes and Tumor Cells", Cytometry, vol. 10, pp. 388–393, 1989.

G. Brugal, et al., "A Double Scanning Microphotometer for Image Analysis: Hardware, Software and Biomedical Applications", J. Histochem. and Cytochem., vol. 27, No. 1, pp. 144–152, 1979.

S.D. Fosså, et al., "DNA Cytomery of Primary Breast Cancer", Acta path. microbiol. immunol. scand. Sect. A, 91:235–243, 1983.

Y. Moustafa, et al., Image analysis of cell proliferation and differentiation in the thymus of the newt Pleurodeles waltlii Michah. by SAMBA 200 cell image processing, Roux's Archives of Developmental Biology, ©Springer–Verlag, 193: 139–148, 1984.

P.F. Mullaney, "Models for Low Resolution Slit Scan Measurements Based On High Resolution Laser Scanning Image Analysis: DNA and Nuclear Dimensions", Pattern Recognition, vol. 13, pp. 49–45, Pergamon Press Ltd., 1981.

P. Strang, et al., "Comparison Between Flow Cytometry an Single Cell Cytophometry for DNA Content Analysis of the Uterine Cervix", Acta Radiologica Oncology 24, pp. 337–341, 1985.

Autofocus Precision, Accuracy and Speed in Automated Scanning

| | Experimental Parameters | | | | | | Phase Contrast | | | | Fluorescence | | | |
|---|---|---|---|---|---|---|---|---|---|---|---|---|---|---|
| | | | | | | | Combined σ | | Max-WA | | Combined σ | | Max-WA | |
| Exp't | Cell Density | Fields | Focus Range | Focus Increment | Time(s)† | Phase/Fluor Function | Max | WA | Mean | σ | Max | WA | Mean | σ |
| 1 | 10% | 1023 | 2.44 | 0.102 | 0.48 | $F_3/F_3$ | 0.210 | 0.097 | 0.002 | 0.059 | 0.160 | 0.057 | 0.003 | 0.041 |
| 2* | 20% | 1239 | 3.52 | 0.195 | 0.38 | $F_3/F_3$ | 0.160 | 0.071 | -0.006 | 0.069 | 0.345 | 0.307 | 0.044 | 0.088 |
| 3 | 30% | 1581 | 3.52 | 0.195 | 0.38 | $F_3/F_3$ | 0.195 | 0.106 | -0.007 | 0.045 | 0.202 | 0.066 | 0.020 | 0.045 |
| 4 | 50% | 1581 | 2.93 | 0.244 | 0.28 | $F_3/F_3$ | 0.093 | 0.041 | 0.014 | 0.027 | 0.101 | 0.093 | 0.001 | 0.011 |
| 5 | 50% | 1581 | 2.93 | 0.244 | 0.28 | $F_3/F_3$ | 0.139 | 0.061 | -0.003 | 0.040 | 0.314 | 0.236 | 0.042 | 0.060 |
| 6 | 60% | 1581 | 2.93 | 0.146 | 0.28 | $F_3/F_7$ | 0.134 | 0.049 | -0.025 | 0.057 | 0.288 | 0.202 | 0.025 | 0.069 |
| 7 | 60% | 1901 | 2.20(P)$ 1.76(F)$ | 0.220(P) 0.073(F) | 0.25(P) 0.48(F) | $F_3/F_7$ | 0.148 | 0.059 | 0.002 | 0.071 | 0.198 | 0.152 | -0.002 | 0.036 |

$ P=Phase; F=Fluorescence

† Time = [number of samples (1+Range/Increment)+video delay(2)+maximum timing delay(2)]/60
* Fluorescence autofocus lost track for a portion of the scan.

Additional notes: All measurements are in microns. The statistics of Max-WA were computed from the means of each set of 20 maxima and weighted averages. Percent Cell Density is an estimate compared to a packed monolayer of cells. σ is the standard deviation.

AUTOFOCUS SYSTEM FOR SCANNING MICROSCOPY

RELATED APPLICATION

This application is a continuation of application No. 08/270,017, filed Jul. 1, 1994, now abandoned, which is a continuation-in-part of application U.S. Ser. No. 08/017,321 filed Feb. 11, 1993, abandoned, which is a file wrapper continuation of U.S. Ser. No. 07/729,383 filed Jul. 12, 1991, which is now abandoned.

STATEMENT REGARDING GOVERNMENTAL RIGHTS

This invention was made with support from the United States Government under Grant No. HL07089-18 awarded by the National Institutes of Health. The Government has certain rights in the invention.

MICROFICHE APPENDIX

A Microfiche Appendix containing computer source code is attached. The Microfiche Appendix comprises one (1) sheet of microfiche having 22 frames, including one title frame.

The Microfiche Appendix contains material which is subject to copyright protection. The copyright owner has no objection to the reproduction of such material, as it appears in the files of the Patent and Trademark Office, but otherwise reserves all copyright rights whatsoever.

BACKGROUND OF THE INVENTION

1. Field of the Invention

The present invention relates to autofocusing and, more particularly, to a system for microscope autofocusing.

2. Description of the Related Technology

Autofocus is a requirement for any fully automated microscope-based image processing system that must scan areas larger than a single field. Experience has shown that it is not possible to maintain focus simply by determining the best foci at two points on a microscope slide and scanning along the line between them in three dimensional space. This may be due to many causes, including mechanical instability of the microscope and irregularity of glass slide surfaces. For example, thermal expansion could account for several microns of instability in microscopes with lamps acting as unevenly distributed heat sources. Using the coefficient of thermal expansion for aluminum, a 1.0° C. increase causes 0.6 micrometer (µm) of expansion for each 25 millimeters (mm) length between the objective and stage in a microscope. Mechanical instability may also arise from gear slippage and settling between moving components in the stage. Microscope slide surface irregularity is another source of error. Standard optical quality mirror flatness is about 1.5 µm over 25 mm. Given that mirrors are ground glass and microscope slides are float glass, microscope slide surface irregularity could be much greater. According to the definition by others, such as Francon (Francon M: Progress in Microscopy, Row, Peterson, Evanston, Ill., 1961), the theoretical microscope depth of field for an objective with numerical aperture (NA) 0.75 is 0.74 µm at a wavelength of 500 nm. Best focus can vary through a range of about 25 µm in a horizontal scan of 50 mm across a microscope slide. Whatever the source of instability, autofocus can compensate given that the positional variations have relatively long time constants.

Most autofocus methods fall into two categories: position sensing and image content analysis. Position sensing methods, such as interferometry, require independent calibration of the best focus location and, more importantly, a single well-defined surface from which to reflect light or sound. In light microscopy there are often two reflective surfaces, the coverslip and slide. In addition, tissue specimens can have significant depth and best focus is not necessarily achieved at the surface of the glass. These problems make absolute position sensing methods impractical for use in light microscopy. Image content analysis functions, such as used by the present invention for autofocusing the microscope, on the other hand, depend only on characteristics measured directly from the image. Best focus is found by comparison of these characteristics in a series of images acquired at different vertical positions. This method of autofocus requires no independent reference and is not affected significantly by the second reflective surface. Its most important limitation is speed, which is dependent on the video rate, the vertical repositioning time, function calculation time and search range.

Image content autofocus functions have previously been compared for brightfield microscopy, but apparently not for fluorescence or phase-contrast microscopy. For example, Groen, Young and Ligthart (Groen F C A, Young I T, Ligthart G: A comparison of different focus functions for use in autofocus algorithms. Cytometry 6:81–91, 1985) compared 11 ; autofocus functions under brightfield using an electron microscope grid and a metaphase spread, and Vollath (Vollath D: Automatic Focusing by Correlative Methods. J Microsc 147:279–288, 1987) tested an autocorrelation function under brightfield using a pearlitic steel specimen. Groen et al. concluded that three autofocus functions, i.e., two gradient functions and the intensity variance, performed the best. However, some autofocus functions that performed well on one specimen did not perform well on others and the authors cautioned against extrapolating the results to other imaging modes and specimens.

The uncertainty in applying autofocus test results from one microscope method to another led to the present invention. The development of the present invention included exploring autofocus performance in microscopy of fluorescent stained biologic specimens. The fluorescent signal can be used directly for autofocus. However, problems summarized by others, such as Chen (Chen L B: Fluorescent labeling of mitochondria, in Fluorescence Microscopy of Living Cells in Culture, Part A, Wang Y L and Taylor D L, eds. Academic Press, San Diego, 103–123, 1989), including photobleaching and the formation of free radicals, singlet oxygen, and heat, can create conditions under which minimizing fluorescent excitation becomes critical. The most critical conditions probably occur in analyzing live cells. If the signal is weak and antiphotobleaching agents cannot be used because of toxicity, the signal could easily be completely lost in the 5–10 video frames of exposure required for autofocus. In addition, the fluorescence byproducts themselves are toxic, and excessive exposure could alter the results or damage living cells. Therefore it is desirable to find a nondestructive imaging technique for autofocus. With brightfield microscopy, fluorescent stained cells appear unstained, showing very little contrast. Phase-contrast microscopy, on the other hand, gives high contrast images of unstained cells and is more useful for autofocus. For these reasons, autofocus function performance was tested for both phase contrast and fluorescence microscopy. More details of different approaches for autofocus can be found in the doctoral dissertation of Jeffrey H. Price entitled *Scanning Cytometry for Cell Monolayers*, University of California, San Diego, 1990, which is hereby incorporated by reference.

SUMMARY OF THE INVENTION

The present solution to the problem of fast and reliable autofocus of cellular components from photosensitive specimens and live cells in a system capable of scanning multiple microscope fields is the instant autofocus system for scanning microscopy designed to automate, simplify, accelerate, and improve the quality of the process. The goal of the autofocus system is to accurately and automatically position the focus positioner, or focus mechanism, of the microscope so as to gather information and present it for further processing.

BRIEF DESCRIPTION OF THE DRAWINGS

FIG. 12 is a chart showing experimental results in autofocus precision, accuracy and speed for the phase contrast and fluorescence methods.

DETAILED DESCRIPTION OF THE PREFERRED EMBODIMENT

The following detailed description of the preferred embodiments presents a description of certain specific embodiments to assist in understanding the claims. However, the present invention can be embodied in a multitude of different ways as defined and covered by the claims.

For convenience, the following description is topicalized into the following principal sections: I. Materials and Methods, II. Metrics for Performance: Autofocus Functions, III. Performance Results, and IV. Conclusions. A more detailed outline of the description is as follows:

I. MATERIALS AND METHODS
  A. Microscope and Image Processor Overview
  B. Microscope and Video Camera
  C. Positioners
  D. Lamps and Exposure Control
  E. Image Processor, Computer and Software
  F. Cells and Specimen Preparation
  G. Basis for Comparison of Autofocus Functions
  H. General Autofocus Process
  I. Binary Search Autofocus Process
  J. Sequential Autofocus Process
  K. Automated Scanning and Real-Time Focus Calculation II. METRICS FOR PERFORMANCE: AUTOFOCUS FUNCTIONS
  A. Functions Based on Resolution
  B. Functions Based on Contrast
  C. Functions Based on Combined Resolution and Contrast
  D. Functions Based on Autocorrelation III. PERFORMANCE RESULTS
  A. Evaluation of Autofocus Functions on Selected Microscope Fields
    1. Microscope Field with Ten Cells
    2. Microscope Field with One Cell
    3. Function Dependence on Magnification and Sampling
  B. Autofocus Performance in Automated Scanning
    1. Accuracy, Precision and Speed
    2. Phase Contrast Focus as an Estimate of Fluorescence Focus

IV. CONCLUSIONS

I. MATERIALS AND METHODS

A. Microscope and Image Processor Overview

Figure 1:
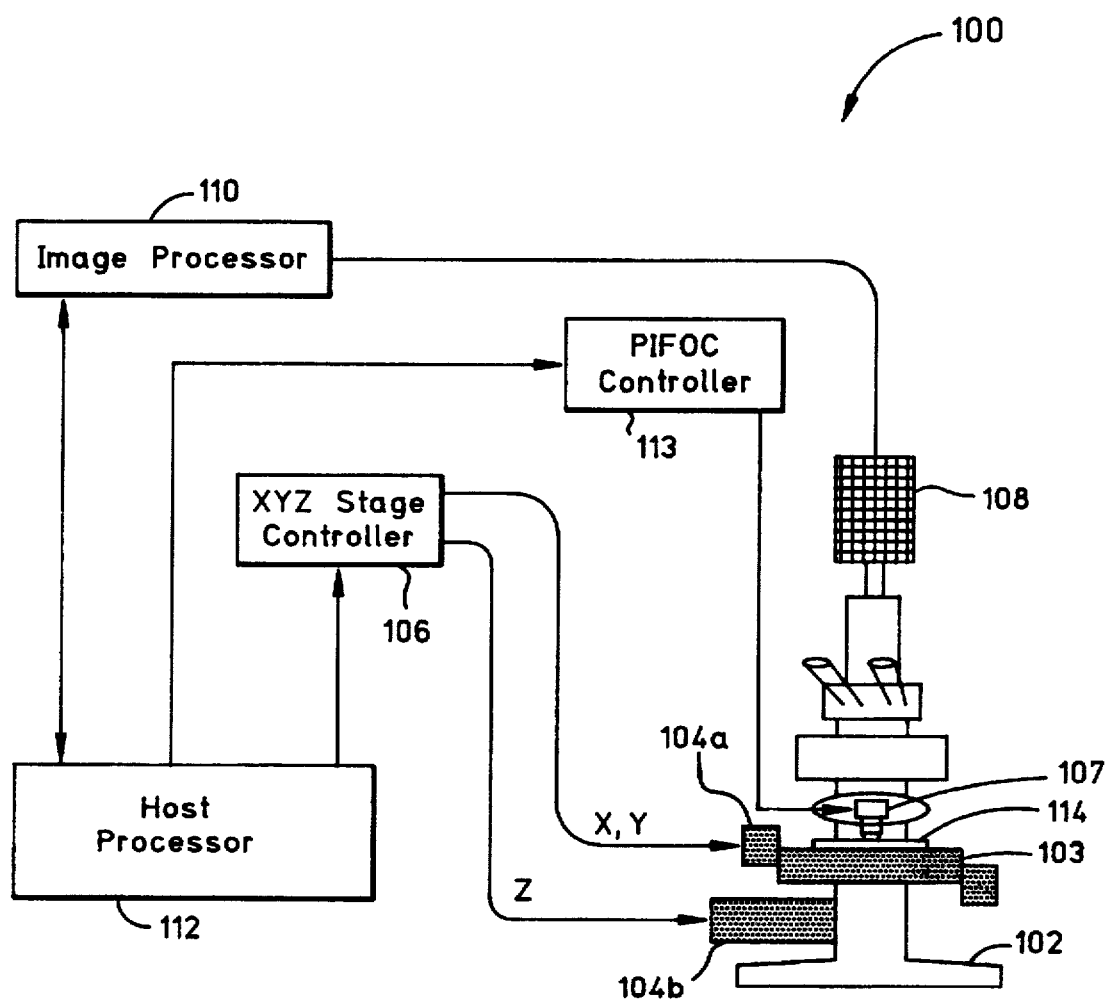
FIG. 1 is a high-level diagram illustrating the basic components of a presently preferred embodiment of the autofocus system of the present invention.

FIG. 1 illustrates the presently preferred embodiment of an autofocus system 100 of the present invention. The hardware components of the system 100 include an epifluorescent microscope 102, a motorized stage 103, controlled by a pair of XY motors 104a and a Z motor 104b, XYZ stage controller 106, a piezoelectric positioner 107, a video camera 108, an image processor 110, and a host processor 112. These components are further described below.

B. Microscope and Video Camera

In one presently preferred embodiment, the cells (FIG. 2) are imaged on a Nikon Optiphot 102 (FIG. 1) through a CF Fluor DL 20× C, 0.75 NA objective with Ph3 phase contrast. This fluorite objective provides high UV transmission. The epifluorescence filter cube has a 365 nm±10 nm (50% of peak) bandpass excitation filter, a 400 nm dichroic mirror and no barrier filter. In experiments, the images were further magnified through a Nikon CCTV 0.9–2.25 zoom lens onto a Dage VE 1000 RS-170 CCD camera 108. Experiments were performed at a zoom of 1.0 except for the sampling experiments, which were carried out at a series of magnifications. For phase contrast, a Nikon 0.52 NA long working distance condenser is used.

C. Positioners

The microscope stage 103 (FIG. 1) is moved laterally under computer control by stepper motors. The stage 103 is built by Syn-Optics (Sunnyvale, Calif.) and modified by New England Affiliated Technologies (Lawrence, Mass.) for finer stepping and simpler computer control. The smallest step size is 0.127 µm. The stage 103 is controlled by a New England Affiliated Technologies 103M microstepping driver and an Oregon Micro Systems, Inc. (Beaverton, Oreg.) PCX AT ISA-bus compatible computer board.

Focus is changed with a piezoelectric objective positioner ("PIFOC") 107 and an E-810.10 closed loop controller (Polytech PI, Costa Mesa, Calif.). The piezo positioner 107 is sandwiched between the objective turret and the objective of the microscope 102. Measurements with an oscilloscope reading the built-in linear variable differential transformer (LVDT) sensor output showed that movements of <1 µm occurred in <10 milliseconds (ms) with the fluorite objective, and response was dependent on objective mass. To retain the 160 mm tube length of the Optiphot 102, the objective turret is replaced by a custom-machined adapter. The 13 mm thick objective positioner significantly reduces image quality if this is not done, but movement through the 100 µm (0.004") range does not measurably degrade the image. Position is controlled by output from a digital-to-analog converter in a Keithley Metrabyte (Taunton, Mass.) DAS-1600 Data Acquisition Board. The 12-bit D/A converter divides the 100 µm range of the PIFOC 107 into 4096 steps of 24 nm each. Due to the previously discussed temperature and mechanical instabilities of the microscope 102 itself, actual focus accuracy is not better than a few microns over long periods, but for the required focus interval of a fraction of a second, the precision approaches the minimum step size.

D. Lamps and Exposure Control

For fluorescent autofocus tests, specimen exposure is controlled with a Uniblitz Model D122 Driver and Shutter (Vincent Associates, Rochester, N.Y.). The fluorescence lamp is an Osram 100w HBO W/2 mercury vapor arc lamp in a Nikon HMX-2 lamp house. Variability of <±3% over 3 hours with this lamp is measured by illumination of the cell stain solution described above, modified by an addition of 10 µg/ml DAPI and 1 mg/ml Herring Sperm DNA (Sigma, St. Louis). This solution is placed in an acrylic well under a sealed coverslip. For phase contrast, exposure is controlled with an EG&G Electro-Optics PS 450AC Power Supply (Salem, Mass.) and an XSA 80-35S-30171 xenon flash lamp (Advanced Radiation Corp., Santa Clara, Calif.). A Nikon HMX-2 lamp house was modified to house the xenon flash lamp and wired to the 450AC power supply. The strobe is triggered by the timer circuit on the data acquisition board. The timing for the strobe is supplied by a vertical blank hardware interrupt from the image processor 110 (FIG. 1). The data acquisition board has a programmable strobe delay that is set for 14 ms to assure that the objective positioner has completed movement prior to image acquisition. The strobe rate is 60 Hertz (Hz) during phase contrast focus testing. The average stability of this lamp is better than the mercury vapor arc lamp, but there are occasional intensity spikes.

To perform an autofocus calculation in real time, either the focus position has to be moved in less than 16 ms (for 60 Hz operation), or the position has to be moved at a constant velocity and the image frozen with a strobe. For the best performance with the incremental movement utilized herein, the image is collected after movement has been completed. This is done in phase contrast by delaying the strobe 14 ms after the vertical blank in the video signal (when the command to change position is sent to the PIFOC 107). This delay insures that the focus position has changed before the image is collected by the video camera 108. The 14 ms delay and the strobe would not be required if the position could be changed during the vertical blank interval of about one ms. Better feedback control electronics on the PIFOC 107 would allow movement to occur fast enough to eliminate the need for the strobe.

E. Image Processor, Computer and Software

Figure 3:
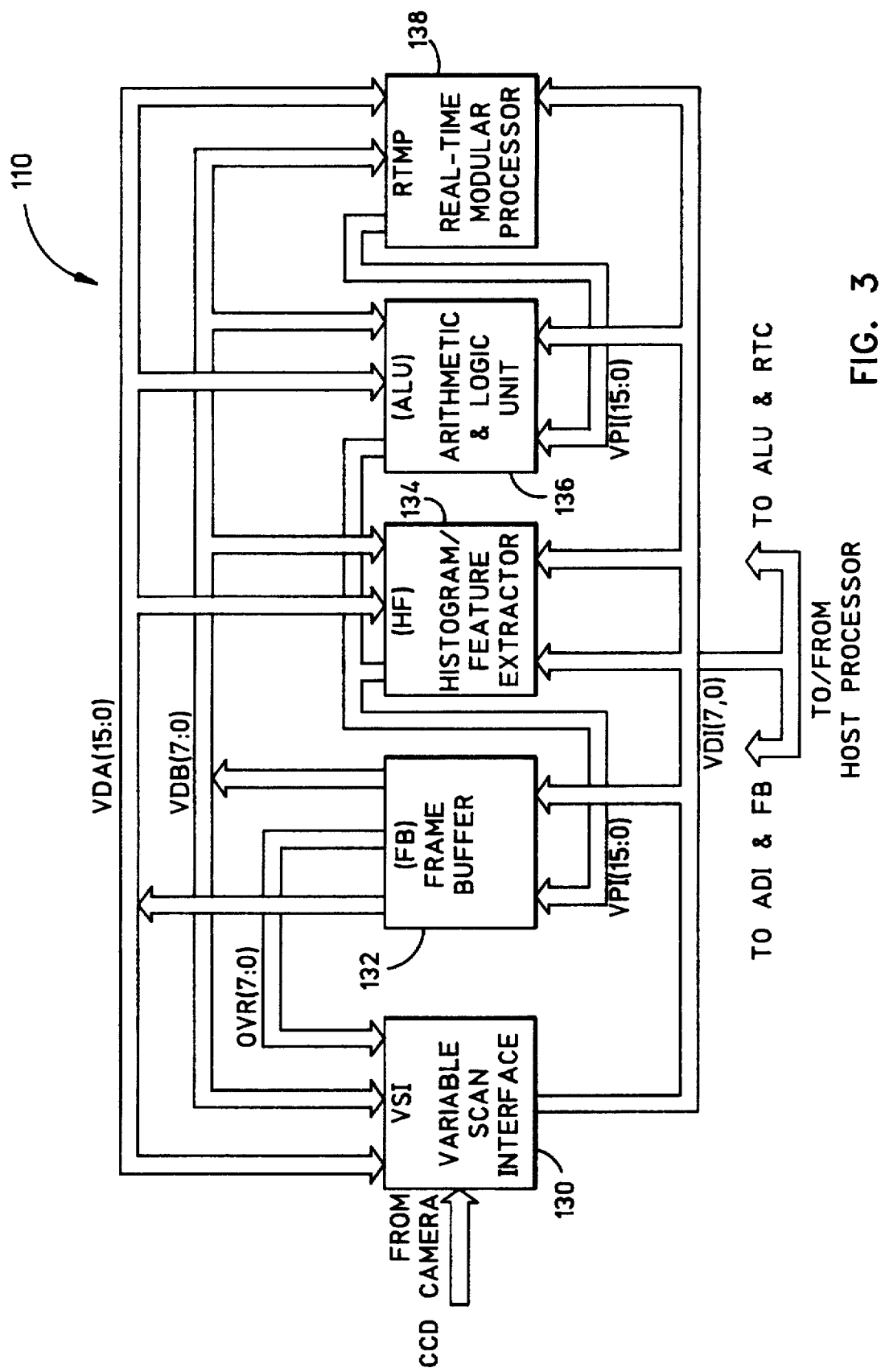
FIG. 3 is a block diagram of the presently preferred image processor of FIG. 1.

An Imaging Technology, Inc. Series 151 Image Processor 110 (FIG. 1) is used for speeding image operations. A block diagram of the preferred image processor 110 is illustrated in FIG. 3. It should be observed that while an image processor 110 will generally speed up the autofocus operation of the present invention, if speed is not critical there is no reason why the calculations performed therein could not take place in the host processor 112 (FIG. 1) or any other computer. The image processor 110 is preferably configured with six functional units, or boards, as follows: 1) a 512×512 8-bit Variable Scan Interface 130 for analog to digital conversion of the video signal generated by the camera 108, 2) a 512×512×32-bit Frame Buffer 132 for storage of four digital images, 3) a 1024×1024×32-bit Frame Buffer (not shown, but similar connections are made to the buses of the processor 110 as shown for the frame buffer 132) for storage of sixteen digital images, 4) a Histogram/Feature Extractor 134 for creating a 10-bit intensity histogram, 5) a Real Time Modular Processor (RTMP) 138 with a Real Time Sobel module for 8×8 convolutions and a 16-bit look-up-table, and 6) an Arithmetic/Logic Unit 136 for multiplication, subtraction, addition and scaling. The RTMP 138 is a single board with three plug-in connections for sub-modules. The Real Time Sobel module utilizes two of these connections and the look-up-table utilizes the third connection. All of these operations proceed at video rates and can be pipelined for parallel operation.

The key components of this system for testing the autofocus functions are the 8×8 convolver (part of RTMP 138) and the histogrammer 134. For most of the autofocus functions, the image is convolved and then histogrammed in a single pipelined video frame or field. The histogram is used to calculate the intensity sum, sum of squares and statistics, e.g., variance or standard deviation, with filtered image results truncated to 8 or 10 bits/pixel. The calculation results are further used to calculate a measure of focus. For 16-bit calculations, the image is first transferred to the host computer. Small differences are sometimes observed between the 8-bit and 10-bit results, but no further improvement is observed utilizing 16-bit results. Therefore, only 10-bit data for autofocus of selected fields is reported. For the presently preferred 60-Hz scanning implementation, the absolute value of the filtered images is taken prior to truncation to 8 bits. The host computer 112 (FIG. 1) is preferably an AT-compatible 33 megahertz (MHz) Intel i486 personal computer (PC).

The software programs to implement the autofocus process (FIG. 4) and related control functions are written in 'C' and assembler. A portion of the 'C' and assembler source code is included in the attached Microfiche Appendix. The C routines are compiled with Metaware High C (Santa Cruz, Calif.). A Phar Lap (Cambridge, Mass.) assembler is used for the interrupt service routines that are running in the background. All object code is linked with the Phar Lap 386 DOS Extender. The Imaging Technology Series 151 C Library source code is also ported to ANSI C and recompiled with Metaware High C. This combination allows use of the full 32-bit capability of the i486 CPU by programs running under 16-bit DOS.

F. Cells and Specimen Preparation

Figure 2:
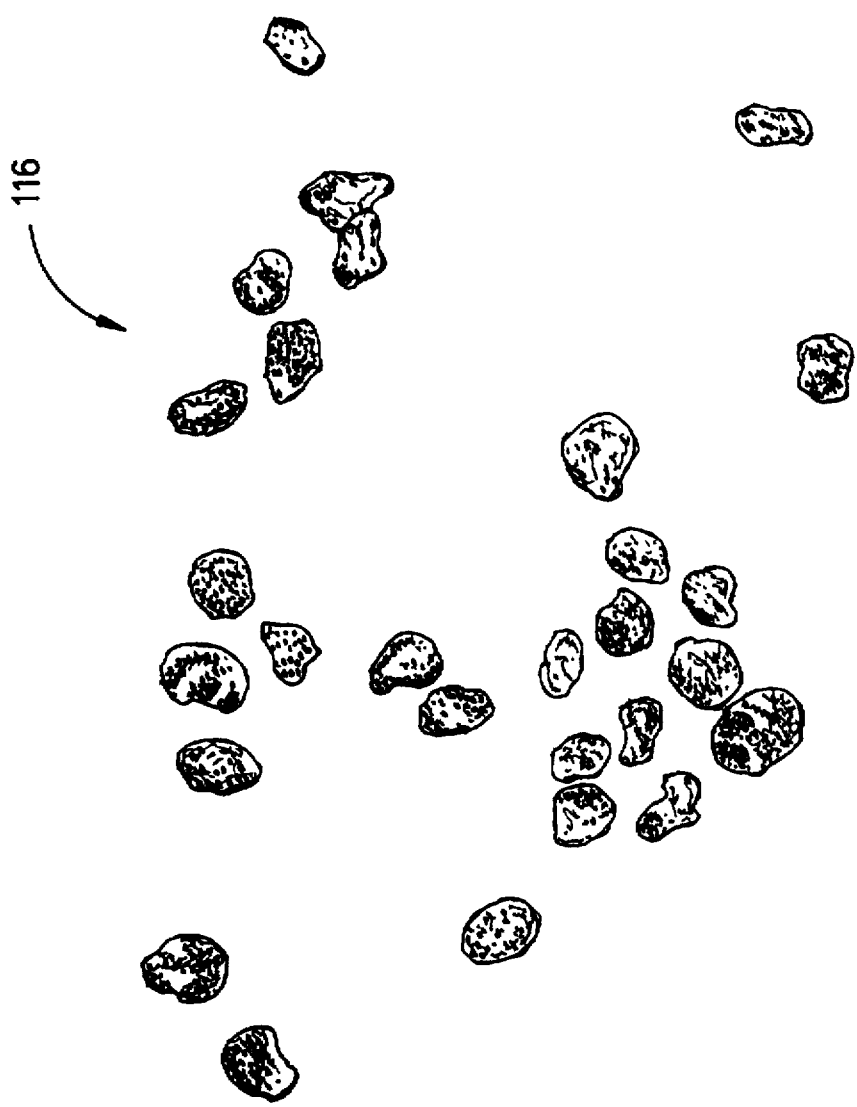
FIG. 2 is a representation of a magnified image of cells as seen through the microscope of the system shown in FIG. 1.

A portion of an example specimen, such as the specimen 114 of FIG. 1, is shown in FIG. 2. FIG. 2 represents a magnified image of a typical specimen comprising a set of cells, particularly cell nuclei, generally indicated at 116.

In one experiment, NIH 3T3 cells were plated on washed, autoclaved #1.5 coverslips. The cells were maintained in Eagle's minimal essential medium with Earle's salts, supplemented with 10% fetal bovine serum, 100 µg/ml gentamicin, and 0.26 mg/ml L-glutamine (final concentrations), in a humidified 5% $CO_2$ incubator at 37° C. After 1 day of cell growth, the coverslips were washed in phosphate buffered saline (PBS), fixed for 10 minutes in 4% paraformaldehyde in 60% PBS, and stained for one hour. The stain solution consisted of 50 ng/ml 4',6-diamidino-2-phenylindole dihydrochloride (DAPI, Molecular Probes, Eugene, OR), 10 mM TRIS, 10 mM EDTA, 100 mM NaCl, and 2% 2-mercaptoethanol as described by others, such as Hamada and Fujita (Hamada S, Fujita S: DAPI Staining Improved for Quantitative Cytofluorometry. Histochem 79:219–226, 1983). After staining, a few drops of DAPI solution were placed on a glass slide, the coverslips were laid face down over the solution, excess solution was wicked away with tissue, and the coverslips were sealed to the slide with nail polish. This stain solution was found to exhibit excellent antiphotobleaching properties. Although photobleaching was avoided with this preparation, the degree of photobleaching can vary markedly with different techniques. This specimen also did not exhibit significant autofluorescence, which if nonspecific and diffuse could degrade performance by reducing contrast.

G. Basis for Comparison of Autofocus Functions

There is no independent standard against which autofocus functions can be tested. Therefore, performance must be rated by comparison. Groen et al., loc. cit., suggests eight criteria for comparing the performance of autofocus functions. These are: 1) unimodality, or the existence of a single maximum or minimum; 2) accuracy, or coincidence of the extremum and best focus; 3) reproducibility, or a sharp extremum; 4) range, or the vertical distance over which the function will unambiguously determine the direction to best focus; 5) general applicability, or the ability to work on different classes of images; 6) insensitivity to other parameters, or independence from influences such as changes in mean intensity; 7) video signal compatibility, or the ability to use the same video signal as is utilized for image analysis; and 8) implementation, that is, it should be possible to calculate the function rapidly.

The first three criteria—unimodality, accuracy and reproducibility—are most important for automated scanning. The range is less important because focus is usually performed on a field immediately adjacent to one where best focus was just calculated. Comparisons of microscope autofocus functions performed by Groen et al., loc. cit., led to the conclusion that the fifth criterion, general applicability for all types of images, cannot necessarily be expected. For a scanning system, however, it is sufficient to require applicability to one microscope imaging method (e.g., phase contrast or fluorescence) for all microscope fields. The seventh criterion, video signal compatibility, is hardware dependent and is easily satisfied. The eighth criterion, implementation, is dependent on computer speed and function complexity.

H. General Autofocus Process

Figure 4:
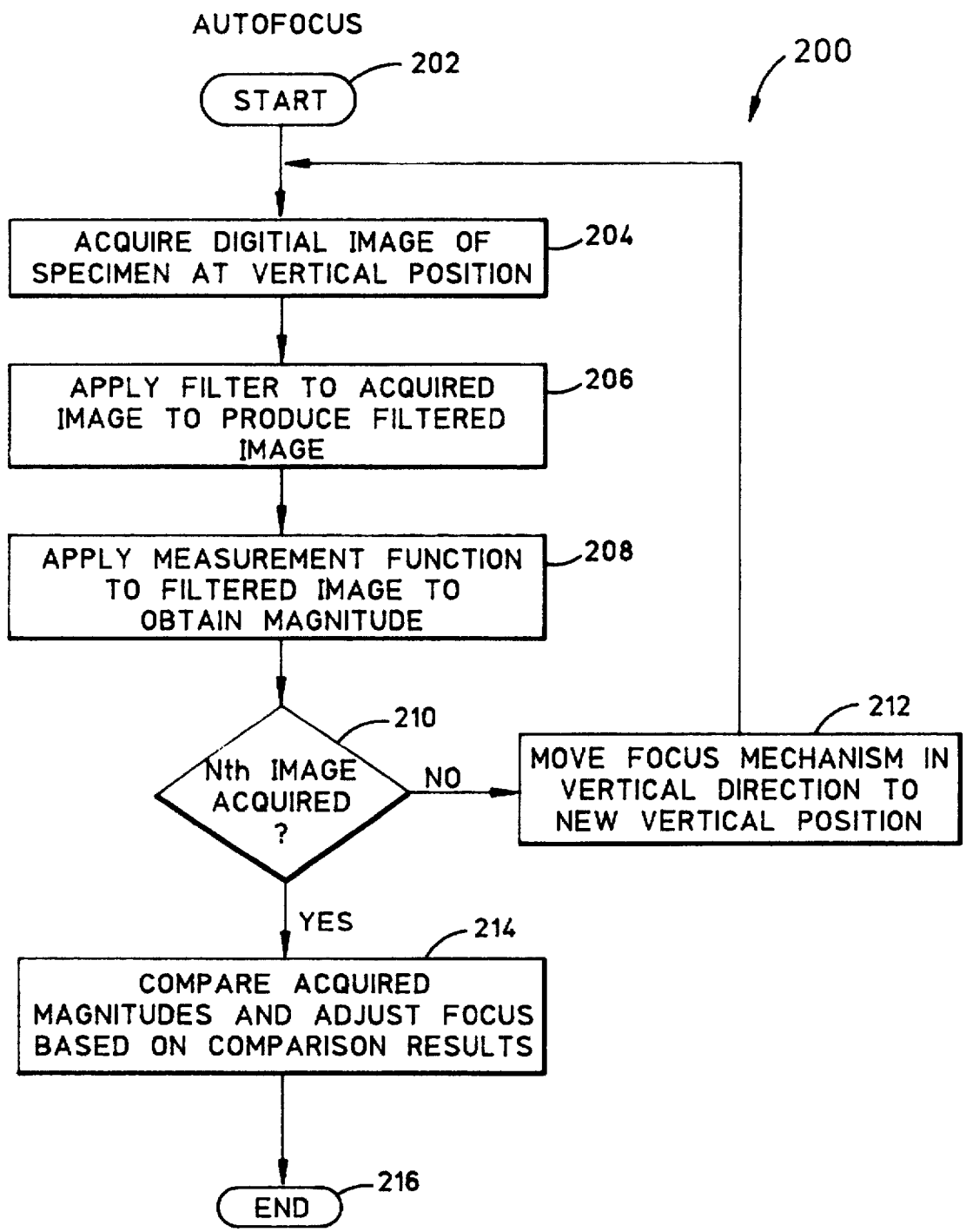
FIG. 4 is a high-level flow diagram of an autofocus process performed by the system shown in FIG. 1.

Referring to FIG. 4, a high-level description of the autofocus process 200 will now be given. Note that autofocus is controlled from the host processor 112 (FIG. 1). The host processor 112, or the image processor 110 under control of the host processor, can perform a transformation on the image and obtain a value which represents a degree of focus. This value can then be compared with another value obtained from another image after the stage 103 is moved up or down via the XYZ stage controller 106 to indicate the next direction of stage movement or after the objective is adjusted by the PIFOC 107.

Beginning at a start state 202, the system 100 proceeds to a state 204 to acquire a digital image of the specimen 114 on the stage 103 at a first vertical position. The image is captured by the image processor 110. Moving to state 206, the system 100 applies a filter to the digital image to produce an intermediate or filtered image. The presently preferred embodiment utilizes a digital filter, and more specifically, the image sharpening transformation defined in function $F_7$ of Table 1. Of course, other filters, including analog filters can be used. Proceeding to state 208, the system 100 applies a measurement function to the intermediate image to obtain a magnitude. The presently preferred embodiment uses a contrast measurement function which utilizes the variance or standard deviation of image intensity, or the sum of the squares of the image intensity. Moving to a decision state 210, the system 100 determines if the Nth image has been acquired. The value of N utilized varies according to the specific autofocus method employed. For the purposes of this discussion, and as an example, N will be equal to two. Therefore, during the first pass of states 204 to 210, only the first image is acquired, and the flow continues at state 212 wherein the stage 103 is moved by Z motor 104b in a vertical direction to a new (second) vertical position. In the preferred embodiment there are two focus mechanisms, therefore the piezoelectric PIFOC positioner 107 is moved instead of the stage 103 for fast autofocus, and both the PIFOC 107 and the stage 103 are to be moved together to combine fast autofocus and extended focus range.

After the stage 103 has been moved to the new vertical position, or the PIFOC 107 adjusts the objective, the flow continues at state 204, wherein a digital image is acquired at the second vertical position. The states 206 and 208 are executed again using the second image to obtain a second magnitude. Moving to state 210, when the Nth image has been acquired, as for the current example of N=2, the system 100 proceeds to state 214. At state 214, the acquired magnitudes are compared and the focus is adjusted based on the results of the comparison. For the current example, if the magnitude at the first vertical position is greater than the magnitude at the second vertical position the focus mechanism is moved toward the first vertical position, else if the magnitude at the first position is less than the magnitude at the second position, the focus mechanism is moved toward the second vertical position. The PIFOC 107 and the vertical stage stepper motor positioner are both focus positioners. The PIFOC is much faster, but has a shorter range (100 µm or 0.004" in the presently preferred model, 200 µm in an alternate embodiment. The stepper motor, moving the entire mass of the stage, rather than just the objective, takes longer and cannot be use din a real time calculation, but has a range limited only by the room between the specimen and objective and the physical design of the microscope. Either or both can be used for autofocus. For a slow system with focus in a few seconds, the stage is fast enough. For a fast system requiring focus in a fraction of a second, the PIFOC 107 is necessary. For applications requiring greater range and fast focus, the stage could be focused first and all subsequent focusing done by the PIFOC 107 until the range is exceeded. The stage could then be adjusted as necessary to keep the PIFOC 107 within its range. After the focus has been adjusted at state 214, the autofocus process 200 completes at an end state 216.

A number of different autofocus functions, which are further discussed below, may carry out one or both of states 206 and/or 208.

The following two section will describe two specific methods utilized for autofocus: binary search and sequential autofocus.

I. Binary Search Autofocus Process

Figure 5:
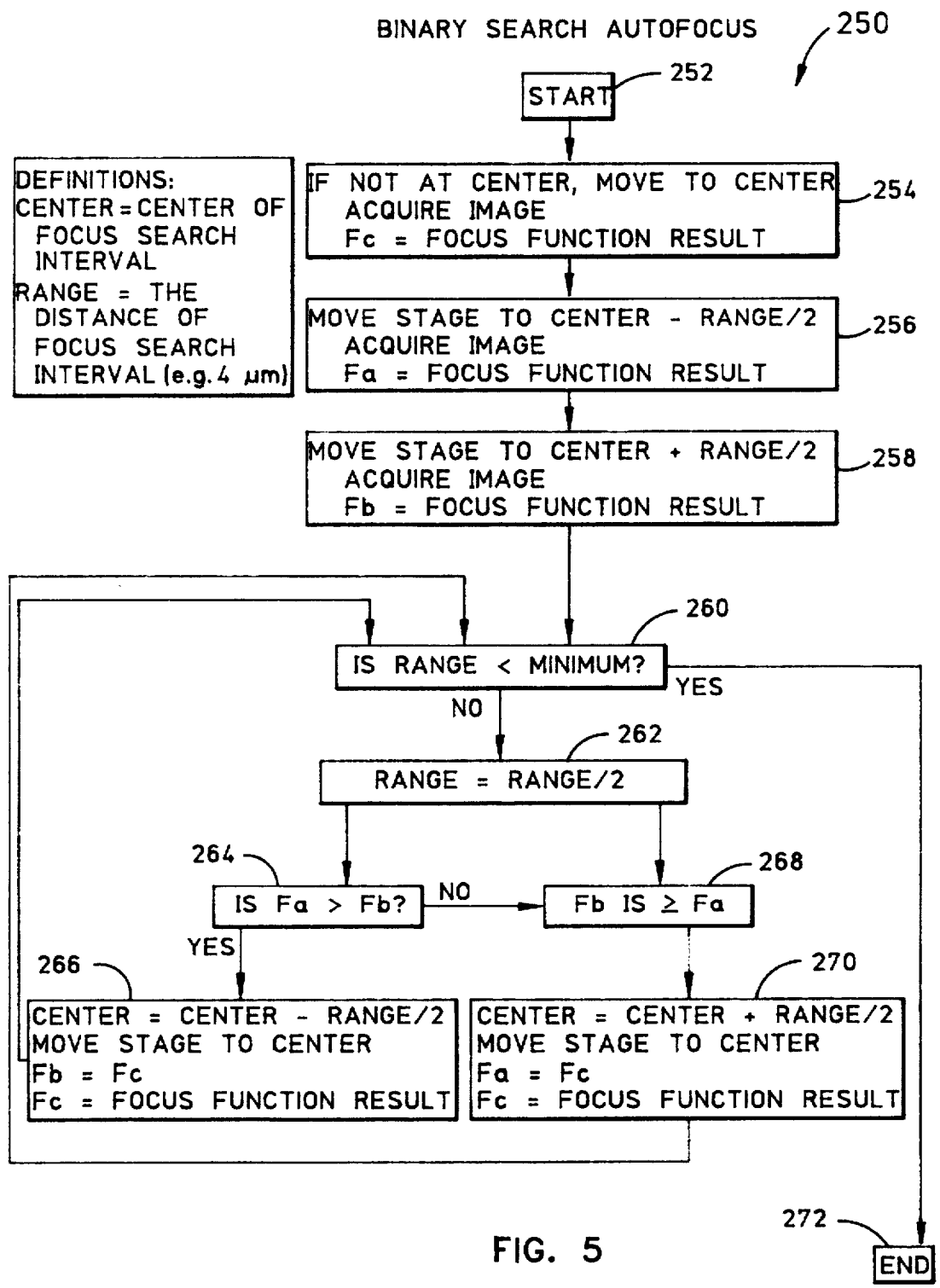
FIG. 5 is a flow diagram of a binary search autofocus process performed by the system shown in FIG. 1.

Referring to FIG. 5, the binary search autofocus process 250 will now be described. This process is a more specific version of the process 200 shown in FIG. 4. Autofocus process 250 uses the well-known binary search algorithm to move the stage 103 (FIG. 1) and locate best focus. The search range is fixed as the distance of focus search interval and the center of the range is the center of focus search interval. Binary search autofocus is carried out by defining two focus positions between which focus is thought to exist and sequentially dividing the range in half to narrow down on best focus. The range is narrowed in this manner until it is smaller than the precision needed to identify best focus.

The binary search autofocus process 250 begins at a start state 252, wherein a user, or an automated scanning program, requests focusing. The range is set to an initial value, e.g., 4 microns. The system 100 then moves to a state 254 wherein the focus mechanism is positioned at the center of the focus test range. The focus mechanism is the PIFOC 107 or the stage 103 (note the vertical control is 104b which moves the stage 103 through a series of gears inside the microscope), or both. An image is then acquired, filtered, and histogrammed by using the image processor 110. From the histogram, a single focus function result (Fc) is calculated for that position and stored. Moving to state 256, the focus mechanism is positioned at the beginning of the range, and another image is acquired, filtered, and histogrammed. Another focus function result (Fa) is calculated and stored as before. Proceeding to state 258, the focus mechanism is positioned at the end of the range, and another image is acquired, filtered, and histogrammed. From the histogram, a single focus function result (Fb) is calculated for that position and stored as before. States 252 through 258 comprise an initialization sequence of the process. The rest of the flow chart states represents the loop that is executed to narrow the range until focus is found.

Continuing at a decision state 260, a check (is range less than minimum) is made to see if the desired precision has been achieved. The minimum is user and application dependent. A practical example of the minimum is between 0.001 µm and 1.0 µm depending on the demands of the application. The minimum step size of the presently preferred PIFOC 107 is 0.024 µm and is determined by the digital/analog converter control board in the host computer 112 and the electronics of the PIFOC controller. If the range is small enough focus has been located, and the flow completes at an end state 272. If the range is not less than minimum, as determined at decision state 260, the system 100 continues at state 262 wherein the range is decreased by half. Proceeding to a decision state 264, a determination is made if the focus value result Fa is greater than the result Fb. If Fa, the focus value at the beginning of the range, is greater than Fb, the focus value at the end of the range, then the focus is closer to the beginning of the range. The new range will be defined by the old beginning and the center. If not, the focus is closer to the end of the range and the new range will be defined by the old center and end.

If Fa is greater than Fb, the system moves to state 266, due to the focus value being closer to the beginning of the old range. The system 100 sets the new center to a position between the center and start of the old range, and moves the focus mechanism to the new center. The system also places the focus value (Fc) at the old center into the storage represented by Fb because this is the new end of the range. The system 100 further acquires, filters, histograms and calculates the focus function value for the new image and stores the result in Fc. At the completion of state 266, the system 100 loops back to decision state 260 to determine if the range is now less than minimum, as previously described.

If Fa is not greater than Fb, as determined at decision state 264 and asserted at state 268, the system moves to state 270, due to the focus value being closer to the end of the old range. At state 270, the system 100 sets the new center to a position between the old center and old end of the range, and moves the focus mechanism to the new center. The system also places the focus value at the old center (Fc) into the storage represented by Fa because this is the new start of the range. The system 100 further acquires, filters, histograms and calculates the focus function value for the new image and stores the result in Fc. At the completion of state 270, the system 100 loops back to decision state 260, as previously described.

J. Sequential Autofocus Process

Figure 6:
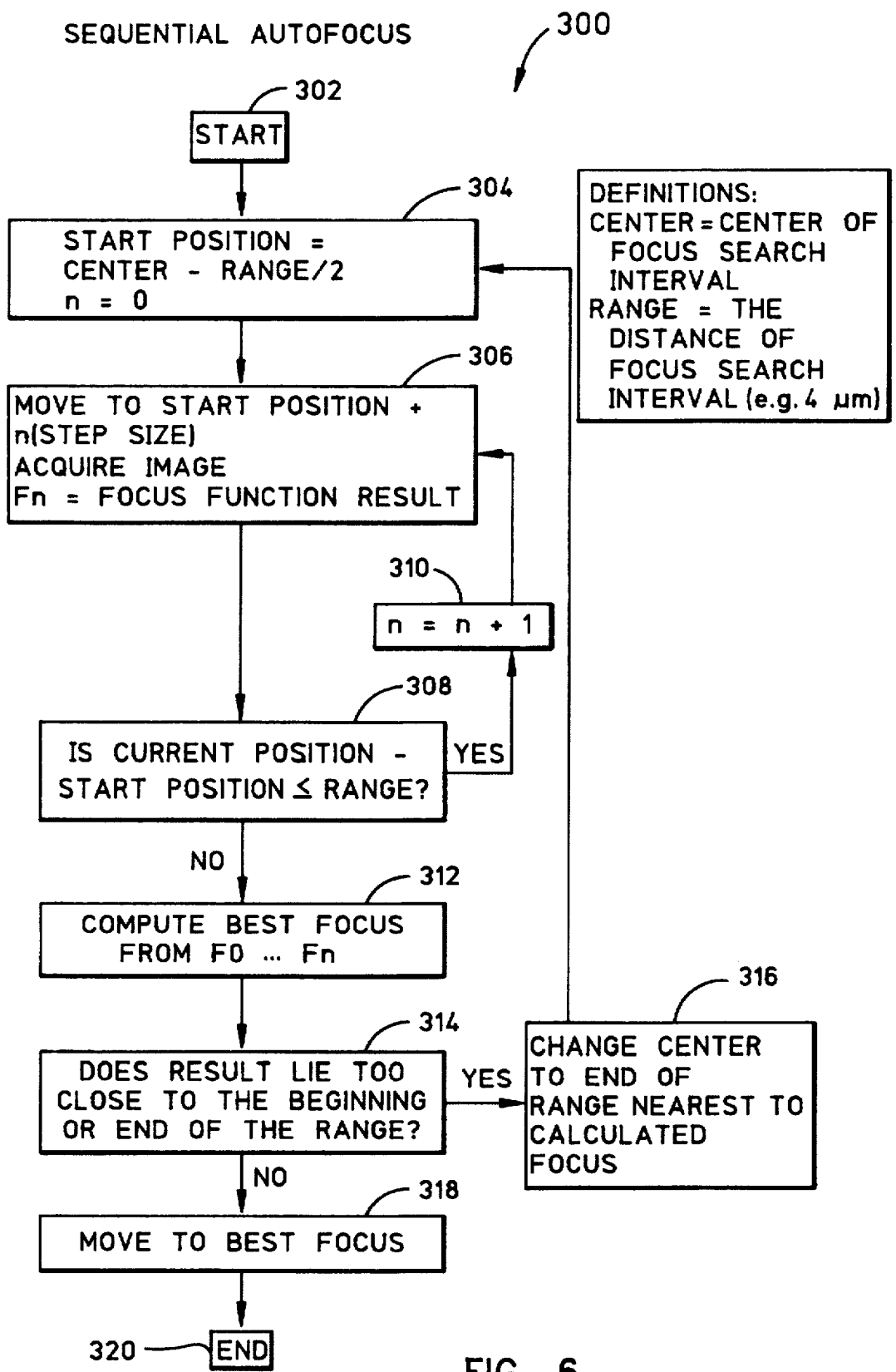
FIG. 6 is a flow diagram of a sequential autofocus process performed by the system shown in FIG. 1.

Referring to FIG. 6, the sequential autofocus process 300 will now be described. The sequential autofocus process 300, which is a more specific version of the autofocus process 200 (FIG. 4), begins at a start state 302, wherein a user, or an automated scanning program, requests focusing. The range is set to an initial value, e.g., 4 microns. The system 100 then moves to a state 304 wherein the start position is set to the initial value at the beginning of the range and the position number, n, is set to 0. Moving to state 306, the system 100 begins a loop (states 306 through 310) that positions the focus mechanism and calculates the focus function at each position. The focus mechanism is positioned to the 'start position plus (n times the step size)'. The step size is the same as the "focus increment" in the experimental table of FIG. 12. Focus increments of 0.102, 0.195, 0.244, 0.146, 0.220 and 0.073 micrometers were used in those experiments. Then the image is acquired, filtered, histogrammed and the focus function calculated. The result is stored for later calculation of best focus. Proceeding to a decision state 308, the system 100 determines if 'the current position minus the start position≦range', i.e., whether the focus position sequence finished. If so, the system moves to state 312 to calculate best focus. If not, the system 100 moves to state 310 to increment the position number, n, by one, and continue moving and calculating the focus function results by looping back to state 306.

If the focus position sequence is finished, as determined at decision state 308, the system 100 moves to state 312 and computes the best focus. The power weighted average equation (Equation 1) is used to compute the best focus from the focus function values at positions 0 to z $F_o \ldots F_z$. At the completion of computing the best focus, the system advances to a decision state 314 to determine if the result lies too close to the beginning or end of the range. One example of too close is within ¼ of the range. If the focus search range is 4 micrometers, and if the focus result were within 1 micrometer of either end of the range, then the center of the range would be repositioned and focus repeated. The actual value may vary depending on the application (specimen, required speed, etc.) . If so, the true focus may lie outside the range. The system 100 proceeds to state 316 to change the center to the end of the range closest to calculated focus and repeat the focus sequence by looping back to state 304, as previously described. Note that the range stays the same, but the process succeeds as long as the focus values increase toward best focus. The range can be broadened automatically to speed finding best focus. This feature is important in an application where the focus at an adjacent field is not known, such as for a commercial microscope focus attachment that focuses regardless of the start position. Best focus is achieved if the result is close to the center, as determined at decision state 314, and therefore the system 100 proceeds to state 318 wherein the focus mechanism is positioned at best focus. The sequential autofocus process 300 completes at an end state 320.

K. Automated Scanning and Real-Time Focus Calculation

One series of tests on the system 100 involved scanning areas of >1000 microscope fields in a raster pattern automatically. At each new field the best focus for the previous field is used for the center of the test focus range. The microscope is refocused at the beginning of the test sequence on each field until the calculated best focus fell into the inner half of the test range. This allows best focus to be achieved even if the best focus is outside the initial test range. In practice, the test range was wide enough to make refocusing rare. Before autofocus, the intensity of the fluorescence image is summed to verify the presence of at least one cell. If no cells are present, the field is skipped. At the beginning of a new row, the best focus from the beginning of the previous row is the center of the test range. Before the start of each experiment, a specimen is placed on the microscope, the scanning rectangle chosen, and the corners of the rectangle checked to verify that the foci are within the 100 µm range. At the first field, focus is performed manually. After the first field there is no human intervention until the scan is complete.

Focus is calculated 20 times for both phase contrast and fluorescence on each field for statistical analysis of repeatability and comparison of accuracy. Precision is evaluated by the combined standard deviation of all focus trials from the entire scan. The combined standard deviation is computed by taking the square root of the average variance. Each focus test sequence is performed at 60 Hz by interrupt service routine control. An interrupt is initiated at the beginning of each vertical blank (60 Hz) by the Variable Scan Interface board on the Series 151 Image Processor. The interrupt service routine controls the strobe, and accounts for the 2 vertical blank delay between image integration on the CCD chip (objective positioner movement) and histogram acquisition on the image processor. Accounting for the delay between positioning and image stabilization enables repositioning and measurement to occur at video rates. The path through the image processor is from the digitized image in the Variable Scan Interface through the convolver to the histogrammer. The histogrammer input contains a 2-bank, 10-bit look-up table that is used to separate the odd and even fields for 60 Hz positioning and function calculation. Histogrammer look-up-table bank 0 is programmed to pass the even field unchanged and bank 1 is programmed to add 256 to the odd field. The interrupt service routine switches banks on alternate vertical blanks. At the end of each odd field the interrupt service routine transfers the resulting 9-bit histogram and independently calculates the odd and even sum, sum of squares and pixel count. These values are placed in arrays accessible to 'C' routines for final calculation of the best focus position. The function results are also normalized by the number of pixels.

After each focus sequence, with evaluation of the function at a number of positions, the maximum and the weighted average are used to find best focus. If the cells had been thinner than the depth of field of the microscope and the discrimination range of the focus function, the maximum would have been expected to perform well. In practice, however, the cells are thicker than the depth of field and much thicker than the discrimination range of the resolution functions (see Results section hereinbelow). Under these conditions, the function result is considered an estimate of the degree of focus at the corresponding position. A fit, or weighted average, of the data was performed during testing. Based on the ideal shape of the focus data, curve fits to a Gaussian and second and third order polynomials were tested. In each case, data were found with relatively aberrant shapes that caused the curve fits to perform very badly. The unusually shaped curves were probably produced by discrete distributions of cellular components in the vertical direction, causing a series of local maxima. For these reasons a weighted average of the form $$W_a = \frac{\sum_z z F_z^n}{\sum_z F_z^n} \qquad (1)$$

where $w_a$ is the weight-averaged position, z is the vertical position (and to be distinguished from a specific function as such notation is used elsewhere herein), F is the result of a preselected autofocus function calculated from an image acquired at one position, and n is the power of the weighing, is used. The power accentuates the peak values. Over a narrow search range of 1 or 2 µm with increments significantly smaller than the depth of field, the function values are similar, and low powers result in best foci that are very close to the average z. To improve sensitivity to the peak value, the power 'n' is increased to 4 and 8 before reasonable sensitivity to the maximum is achieved. These steps are shown in the flowchart of FIG. 6 and are explained above.

Sequential autofocus has an advantage over binary autofocus. Each focus position tested is defined before the focus routine begins. There is no dependence on the focus function value at previous positions. Therefore, delays, such as between integration of the image on the video camera 108 and digitization in the image processor 110, do not slow execution of the focus routine as much as they would with the binary search.

In sequential autofocus, the focus position is moved to a series of locations, and at each location the image is acquired, filtered, and histogrammed. Based on the histogram, a single focus value is calculated and stored. When the focus test sequence is complete, a power-weighted average of the focus function values is used to calculate best focus. Unlike binary autofocus, the calculated best focus position may lie in-between the tested positions.

Both of autofocus methods assume that focus lies within a predetermined range. Most of the time, this is true in scanning microscopy because each new field is directly adjacent to the previous one. If best focus lies at or near the ends of the range, the probability that it actually lies outside the range is higher. In the sequential autofocus method, if the best focus does lie close to the ends, the range is moved and autofocus process is repeated.

II. METRICS FOR PERFORMANCE: AUTOFOCUS FUNCTIONS

Image content autofocus functions are based on the assumptions that images increase in contrast and resolution (edge sharpness) as focus improves. In the contrast model, with an image that consists of light and dark regions, the light regions become darker and the dark regions become lighter as the equipment is moved farther from focus. This change in contrast can be described mathematically by the change in variance or standard deviation of pixel intensity. In the resolution model, detail blurs as the image moves out of focus. Resolution can be measured by analyzing the Fourier frequency spectrum or by the application of gradient, or highpass filters that isolate the high frequencies. The magnitude of the high frequencies or gradients can then be used as a measure of resolution, which is defined as a maximum at best focus. The effects of the defocusing on the optical transfer function have been discussed by others, such as Born and Wolf (Born M, Wolf E: Principles of Optics, 6th Edition, Pergamon Press, New York, 1989), Erteza (Erteza A: Sharpness index and its application to focus control. Appl Opt, 15:877–881, 1976; Erteza A: Depth of convergence of a sharpness index autofocus system. Appl Opt 16:2273–2278, 1977), Goodman (Goodman J W: Introduction to Fourier Optics. McGraw-Hill, New York, 1968), Groen et al., loc. cit., and Hopkins (Hopkins H H: The frequency response of a defocused optical system. Proc Roy Soc A 231:91–103, 1955). Vollath, loc. cit., 1987, and (Vollath D: Verfahren und Einrichtung zur automatischen Scharfein-stellung eines jeden Punktes eines Bildes. German Patent DE 2.910,875 C 2, U.S. Pat. No. 4,350,884, 1982, European Patent 0017726) derived additional autofocus functions based on autocorrelation and then suggested modifications for reducing the effects of noise.

The eleven autofocus functions that were tested are summarized in Table 1, along with references and calculation times on the computer hardware used here. The functions are divided into the following groups: 1) measures of resolution ($F_1$–$F_4$), which are the sum of the squares of the result of a highpass filter; 2) measures of contrast ($F_5$, $F_6$), represented by intensity variance or standard deviation, 3) combined measures of resolution and contrast ($F_7$, $F_8$), and 4) autocorrelation functions ($F_9$–$F_{11}$), which also incorporate components of resolution and/or contrast. The theory supporting the referenced functions is discussed by the respective authors. For mathematical description of these functions, the image is represented by $g_{ij}$ where i and j are the spatial coordinates and g is the pixel intensity and all sums are double over i and j. In the equations, the dependence of the image and the autofocus function on vertical position is assumed (i.e., a function value is calculated from the image at each position).

TABLE 1

Autofocus Functions

| Function | Calculation Time[†] Frames/Position |
|---|---|
| 1. Resolution | |
| $F_1 = \sum_{ij} ([1\ 0\ -1] * g_{ij})^2$ | 1 |
| $F_2 = \sum_{ij} ([1\ -1] * g_{ij})^2$ | 1 |
| $F_3 = \sum_{ij} ([-1\ 2\ -1] * g_{ij})^2$ | 1 |

TABLE 1-continued

Autofocus Functions

| Function | Calculation Time[†] Frames/Position |
|---|---|
| $F_4 = \sum_{ij} \left( \begin{bmatrix} -1 & -2 & -1 \\ -2 & 12 & -2 \\ -1 & -2 & -1 \end{bmatrix} * g_{ij} \right)^2$ | 1 |
| 2. Contrast | |
| $F_5 = \sigma^2 = \frac{1}{n(n-1)} \left( n \sum_{ij} g_{ij}^2 - \left( \sum_{ij} g_{ij} \right)^2 \right)$ | 1 |
| $F_6 = \sigma$ | 1 |
| 3. Resolution and Contrast | |
| $F_7 = \frac{1}{n(n-1)} \left( n \sum_{ij} p_{ij}^2 - \left( \sum_{ij} p_{ij} \right)^2 \right)$ | |
| where $p_{ij} = \begin{bmatrix} -1 & -1 & -1 \\ -1 & 9 & -1 \\ -1 & -1 & -1 \end{bmatrix} * g_{ij}$ | 1,5[††] |
| $F_8 = \sqrt{F_7}$ | 1,5[††] |
| 4. Autocorrelation | |
| $F_9 = \sum_{ij} g_{ij}^2 - \sum_{ij} g_{ij} g_{i+1,j}$ | 4 |
| $F_{10} = \sum_{ij} g_{ij} g_{i+1,j} - \sum_{ij} g_{ij} g_{i+2,j}$ | 8 |
| $F_{11} = \frac{1}{n(n-1)} \left( n \sum_{ij} g_{ij} g_{i+1,j} - \left( \sum_{ij} g_{ij} \right)^2 \right)$ | 8 |

*Convolution operation.
n = i · j, the total number of pixels in the image.
[†]RS-170 video format, '1' corresponds to calculation at the same rate as A/D conversion, 1 frame = 33 ms, 1 field = 16 ms.
[††]1 frame time if convolution result is absolute value truncated to 8 bits, and 5 frame times if 16-bit signed All of these functions utilize the entire image, rather than only the cells. In fluorescence, the cells, or objects, could be roughly identified using a threshold, and focus calculated from only the object pixels. This would add complexity, however, and slow autofocus. Since positioning is 2 fields ahead of function calculation, interposing the requirement to threshold the features and build a mask would cause a delay of at least a few frames. There could also be other problems. The distinct, bright nucleus becomes a dim, amorphous blur away from best focus. Even when this dim blur is barely discernible by eye, the direction to best focus can be easily determined by the algorithm used here. This is true well below the intensity where thresholding would yield a reliable object. Also, the apparent object size increases out of focus, so thresholding at one position would not yield the same set of object pixels as thresholding at another. In phase contrast, segmentation of the cell features from image background would be much more difficult than a simple threshold, especially with the image out of focus. In preliminary experiments, it was observed that even with no cells in the field, the presence of small amounts of cellular debris was enough to keep the system in focus. This is probably because the large number of pixels dramatically improves the signal-to-noise ratio. For these reasons, it is advantageous to utilize the entire image for focus calculation.

Independence from changes in illumination is desirable. For phase contrast, the result at each position was divided by the mean or the square of the mean intensity, matching the order of the function dependence on intensity, to compensate for lamp fluctuations. For fluorescence, such a scaling is ill-behaved because mean intensity nears 0 not far from focus and it is a better measure of focus than of lamp intensity. Therefore, the functions were not similarly scaled for fluorescence autofocus. To correct for lamp fluctuations in fluorescence, independent measurement of lamp intensity are required.

The tested autofocus functions were chosen based on evaluations by other investigators and available computer hardware. Functions such as the thresholded absolute gradient and the thresholded video-signal content by Mendelsohn and Mayall (Mendelsohn M L, Mayall B H: Computer-oriented analysis of human chromosomes-III focus. Comput Biol Med 2:137–150, 1972) were not tested because performance was shown by Groen et al., loc. cit., to depend in part on the arbitrary choice of a threshold. The entropy function, such as described by Shannon (Shannon C E: A mathematical theory of communications. Bell Sys Tech J 27:379–423, 623–656, 1948) was shown by Firestone et al. (Firestone L, Cook K, Culp K, Talsania N, Preston K: Comparison of autofocus methods for automated microscopy. Cytometry 12:195–206, 1991) to be multimodal. Firestone et al., loc. cit., also tested the log spectral moment and two cellular logic functions that were not chosen because of hardware considerations. The log spectral moment requires the Fourier transform, which is still expensive to calculate at or near real time, and the cellular logic functions require different hardware than was available here for fast implementation. Variations of highpass filtering have also been implemented in analog circuitry by others, such as Dew, King and Mighdoll (Dew B, King T, Mighdoll D: An automatic microscope system for differential leukocyte counting. J Histochem Cytochem 22:685–696, 1974) and Johnson and Goforth (Johnson E, Goforth L J: Metaphase spread detection and focus using closed circuit television. J Histochem Cytochem 22:536–545, 1974).

A. Functions Based on Resolution

Groen et al., loc. cit., reported $F_1$, $F_2$, and $F_5$ to be the best of 11 functions tested for brightfield microscopy. $F_1$, the squared gradient function described by others, such as Brenner et al. (Brenner J F, Dew B S, Horton J B, King T, Neurath P W, Selles W D: An automated microscope for cytologic research. J Histochem Cytochem 24:100–111, 1976), Erteza, loc. cit., and Muller and Buffington (Muller R A, Buffington A: Real-Time Correction of Atmospherically Degraded Telescope Images Through Image Sharpening. J Opt Soc Am 64:1200, 1974), is an implementation of the first derivative of the image intensity. In spectral terms, this is a bandpass filter that enhances frequencies just below the highest in the image. Squaring the sum magnifies the differences between function values.

$F_2$ is the 1D Laplacian also described by Erteza, loc. cit., and Muller and Buffington, loc. cit. This filter is a measure of the second derivative of the image intensity. By operating on immediately adjacent pixels, $F_2$ has more predominant highpass frequency characteristics than $F_1$, measuring resolution at a smaller scale. A variation of the Laplacian, based on lateral inhibition in the eye, was also evaluated by others, such as Harms and Aus (Harms H, Aus H M: Comparison of digital focus criteria for a TV microscope system. Cytometry 5:236–243, 1984). $F_3$ is the sum of the squares of the difference filter as described by Erteza, loc. cit., and Muller and Buffington, loc. cit. By operating on both immediately adjacent pixels, $F_3$ has the most predominant highpass frequency characteristics and measures resolution at the smallest scale. The use of similar derivative filters is explored by others, such as Shazeer and Harris (Shazeer D, Harris M: Digital Autofocus Using Scene Content, in Architectures and Algorithms for Digital Image Processing II. SPIE 534:150–158, 1985). $F_4$, a common 2D Laplacian not previously tested, was added for comparison. With square pixels, $F_4$ would have been a mixture of the highest frequencies, corresponding to the horizontally and vertically adjacent pixels, and the next highest frequencies, corresponding to the diagonally adjacent pixels. With the rectangular pixels and larger vertical sampling period of the RS-170 camera, however, this filter mixed in lower frequencies and did not have a higher frequency response than $F_3$.

B. Functions Based on Contrast $F_5$, the statistical variance of the intensity as a measure of contrast, was proposed by, for example, the Kernforschungszentrum Karlsruhe GmbH (Kernforschungszentrum Karlsruhe GmbH: Verfahren und Einrichtung zur Automatischen Scharfeinstellung eines jeden Bildpunktes eines Bildes. Patent Specification PLA 7907 Karlsruhe, 1979). $F_6$ is the standard deviation of the intensity, or the square root of $F_5$. It should be noted that under some conditions contrast achieves a local minimum, rather than a maximum, at best focus. The interference fringes that cause this are more commonly observed in transmission electron microscopy. With the light microscope, one way to observe this phenomenon is by using phase contrast to image a micrometer (e.g., 0.85 NA 40× objective and 10 µm spacing). Best focus is at a local contrast minimum, and interference produces a series of contrast maxima and minima as focus is changed. Thus, contrast as a measure of focus must be utilized with caution in specimens with nonrandom spacing viewed in brightfield microscope modes.

C. Functions Based on Combined Resolution and Contrast $F_7$ and $F_8$ combine the variance and standard deviation, respectively, and a 3×3 sharpening filter. As pointed out by others, such as Vollath (Vollath D: The Influence of the Scene Parameters and of Noise on the Behavior of Automatic Focusing Algorithms. J Microsc 152(2):133–146, 1988), the frequency spectrum is independent of the variance. That is, the variance can be changed by scaling the intensities without altering the relative Fourier power spectrum. The converse is not true: filtering the image can change the contrast. Thus, the image statistics measure a property fundamentally different from the Fourier spectrum, or sharpness of the image. This suggested using the variance (or standard deviation) as the basic autofocus measure and modifying the frequency effect by prefiltering the image. The fact that hardware capable of calculating the variance of a filtered image at video rates is becoming common makes consideration of this class of autofocus functions appropriate.

D. Functions Based on Autocorrelation

Correlation can be used to align images by multiplying them at different relative shifts and summing the resulting pixels. A maximum occurs when the images are correctly aligned. Similarly for autofocus, if an image is multiplied by itself shifted $D_i$, $D_j$, a maximum in the correlation function occurs at $D_i=0$, $D_j=0$. Vollath, loc. cit., 1987 and 1982, pointed out that if the correlation function at $D_i=0$, $D_j=0$ is compared with the correlation function with the image shifted with respect to itself, say $D_i=1$, $D_j=0$, the difference increases as image contrast increases. Therefore a maximum in the correlation function, $F_8$, should occur at best focus. Vollath, loc. cit., 1988, then made analogies between $F_8$ and the variance, $F_3$, to obtain $F_9$ and $F_{10}$. These correlation functions apparently have not been previously tested on biologic microscope images.

III. PERFORMANCE RESULTS

To determine the suitability of the various functions using the sequential autofocus process of FIG. 6, each was first tested on selected microscope fields for both phase contrast and fluorescence microscopy. In preliminary experiments it was noted that the shapes of the focus function plots were dependent on the number of cells in the field. In particular, it was found that a field containing a single small cell produced significantly different results than a field containing several cells. For this reason tests were performed on both types of fields. It was also found that the results were dependent on magnification, even using the same objective. Therefore, tests were performed at a series of magnifications by changing the zoom on the relay lens. From these experiments on selected fields, functions were chosen for phase contrast and fluorescence autofocus, compared in experiments scanning many fields and evaluated for accuracy, precision, reliability and speed.

A. Evaluation of Autofocus Functions on Selected Microscope Fields

1. Microscope Field with Ten Cells

Figure 7A:
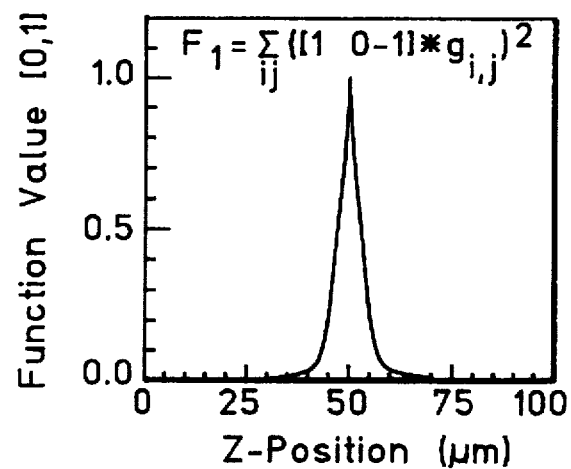
FIGS. 7a, 7b, 7c, 7d, 7e, 7f, 7g, 7h, and 7i illustrate autofocus function ($F_1$–$F_{11}$) results for a microscope field containing 10 fluorescent stained cells using the system shown in FIG. 1.
Figure 7B:
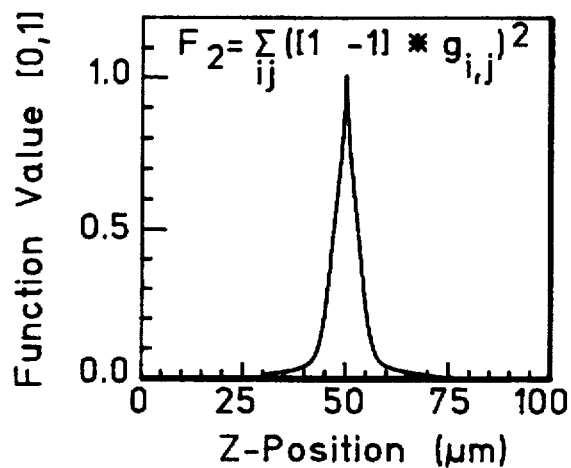
Figure 7C:
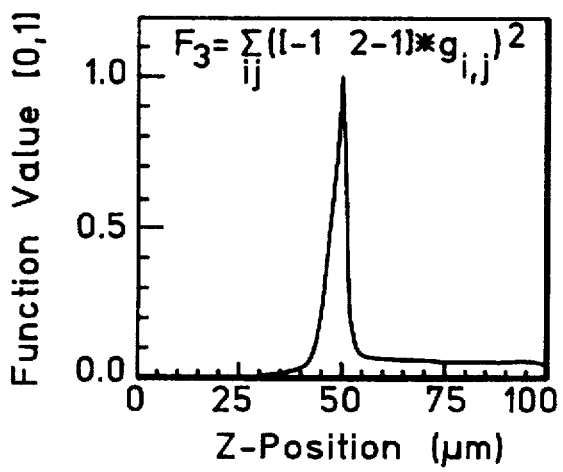
Figure 7D:
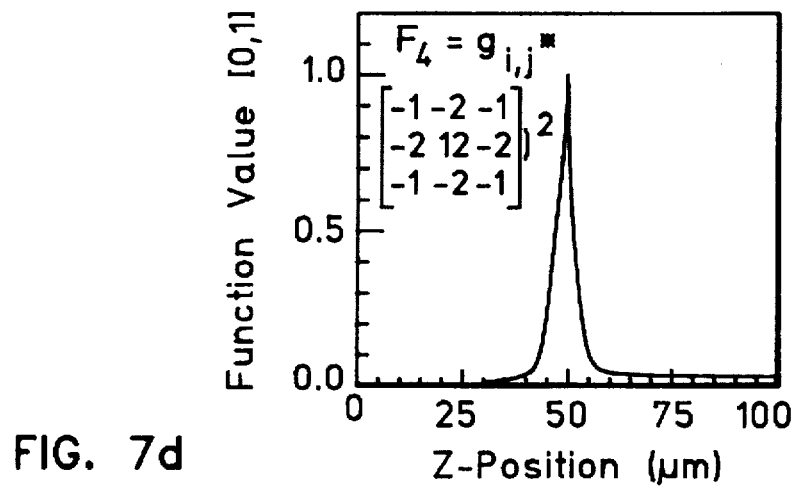
Figure 7E:
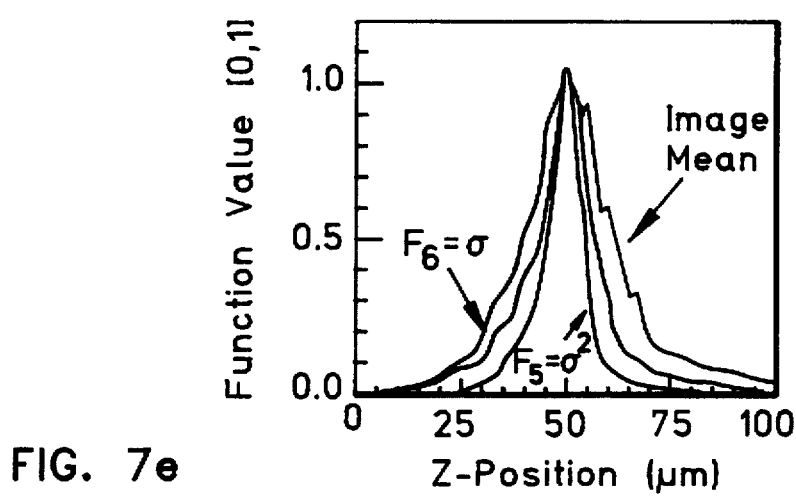
Figure 7F:
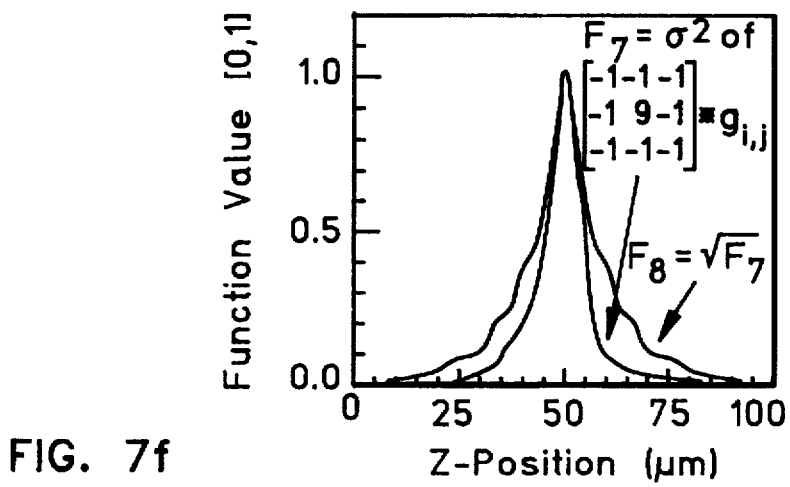
Figure 7G:
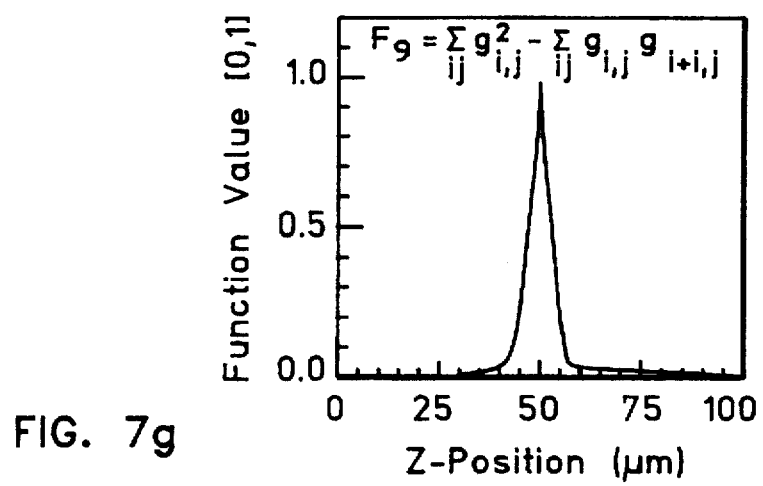
Figure 7H:
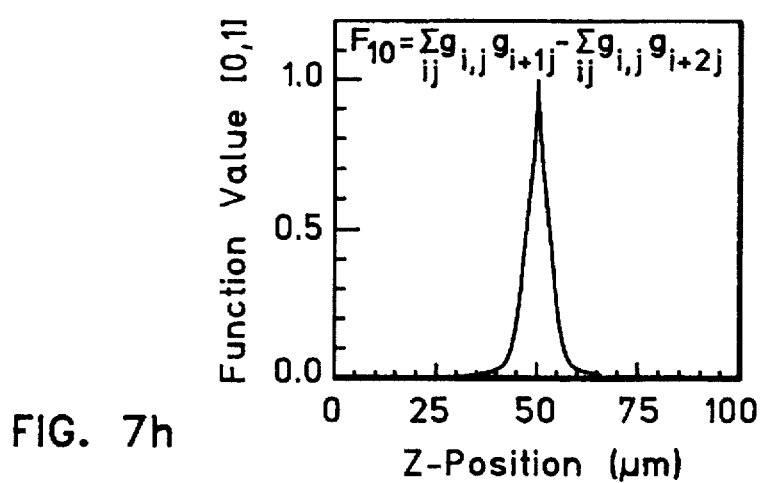
Figure 7I:
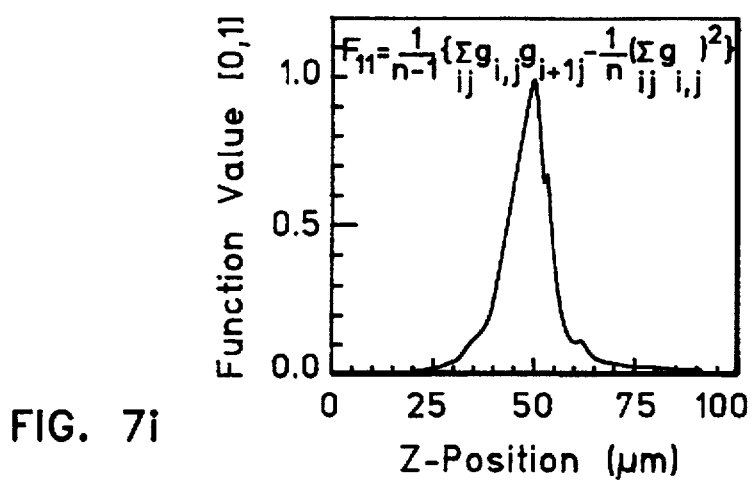
Figure 8A:
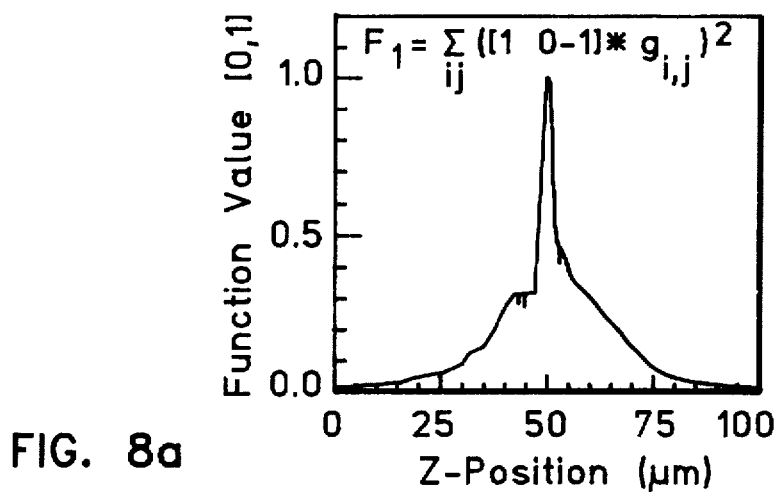
FIGS. 8a, 8b, 8c, 8d, 8e, 8f, 8g, 8h, and 8i illustrate autofocus function ($F_1$–$F_{11}$) results for a phase contrast microscope field containing 10 cells using the system shown in FIG. 1.
Figure 8B:
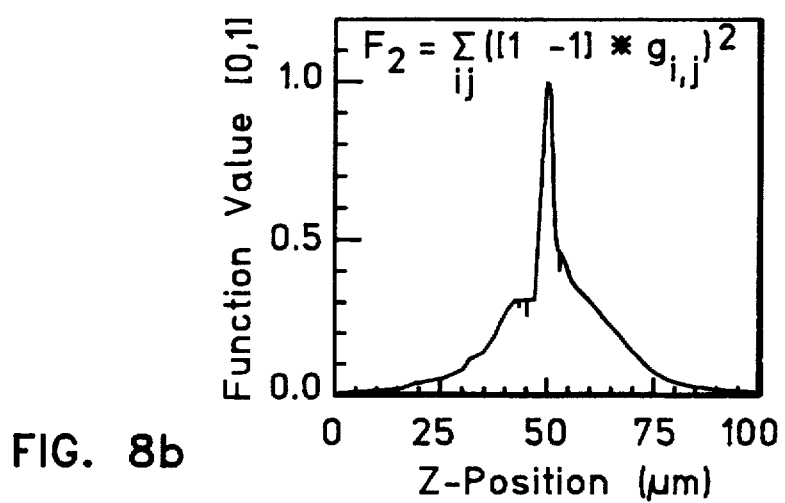
Figure 8C:
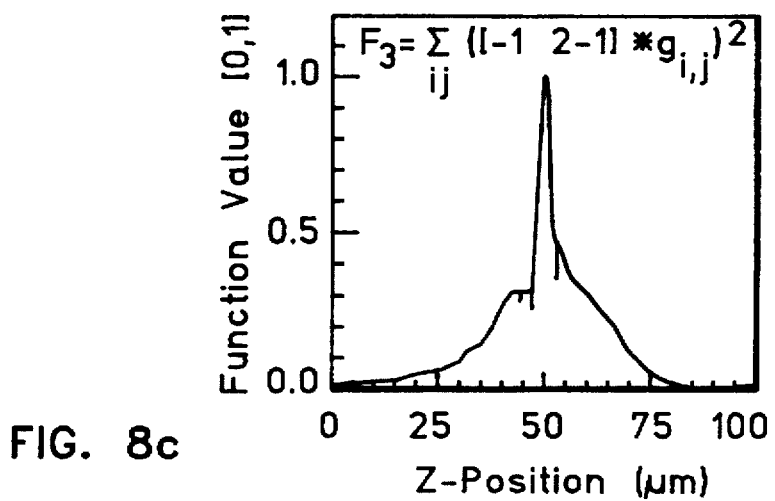
Figure 8D:
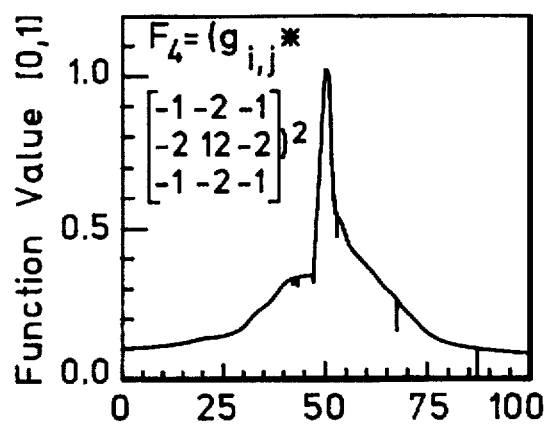
Figure 8E:
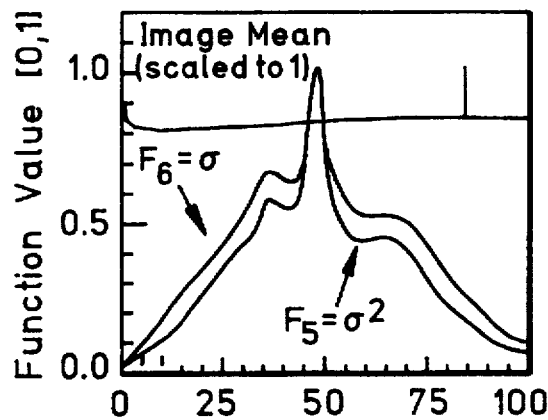
Figure 8F:
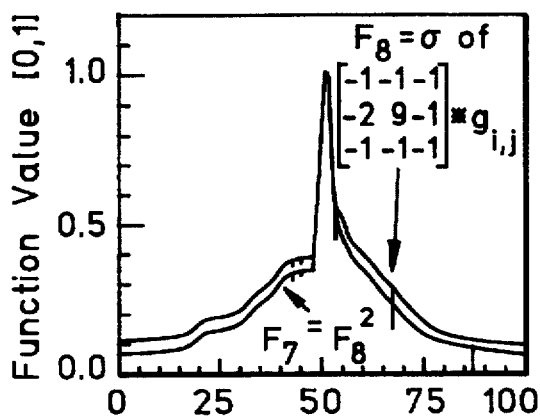
Figure 8G:
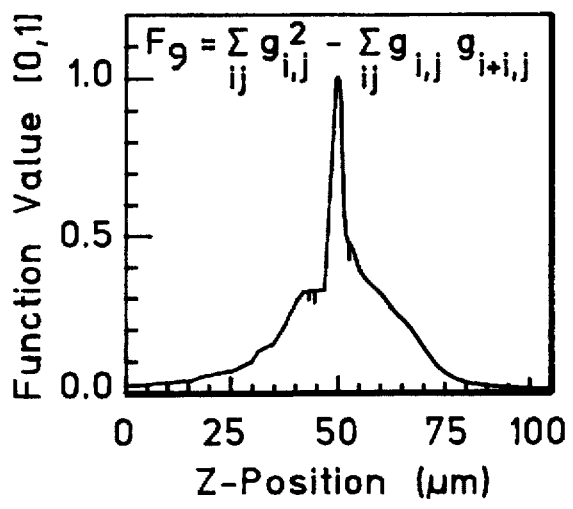
Figure 8H:
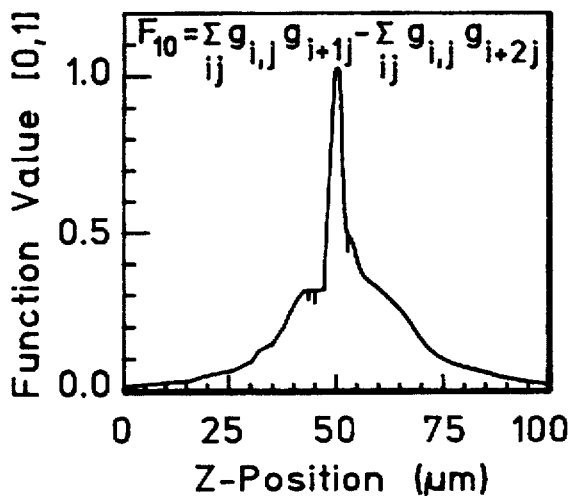
Figure 8I:
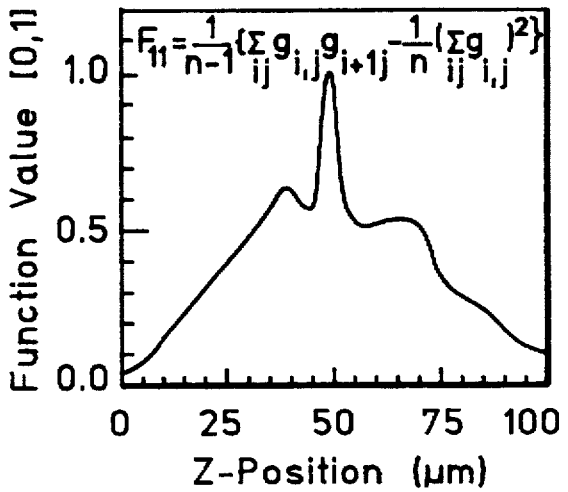
Figure 9A:
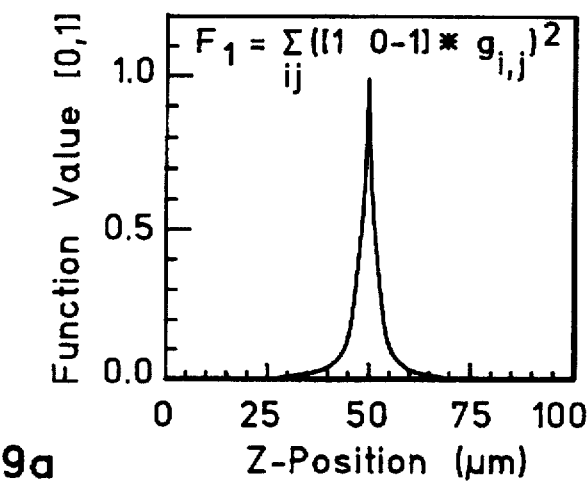
FIGS. 9a, 9b, 9c, 9d, 9e, 9f, 9g, 9h, and 9i illustrate autofocus function ($F_1$–$F_{11}$) results for a microscope field containing a single fluorescent stained cell using the system shown in FIG. 1.
Figure 9B:
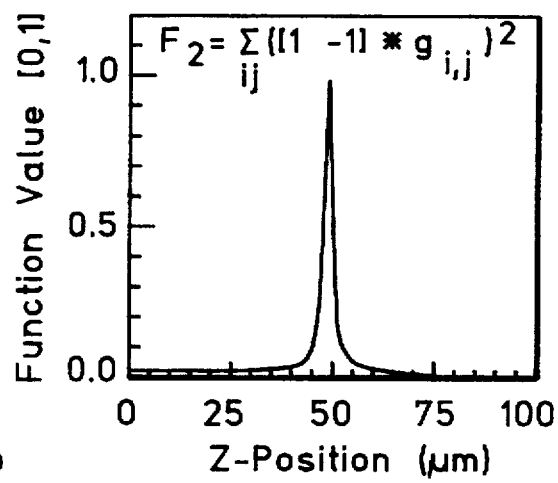
Figure 9C:
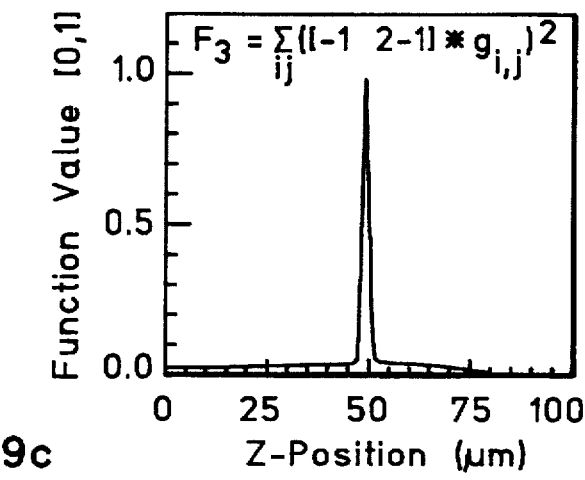
Figure 9D:
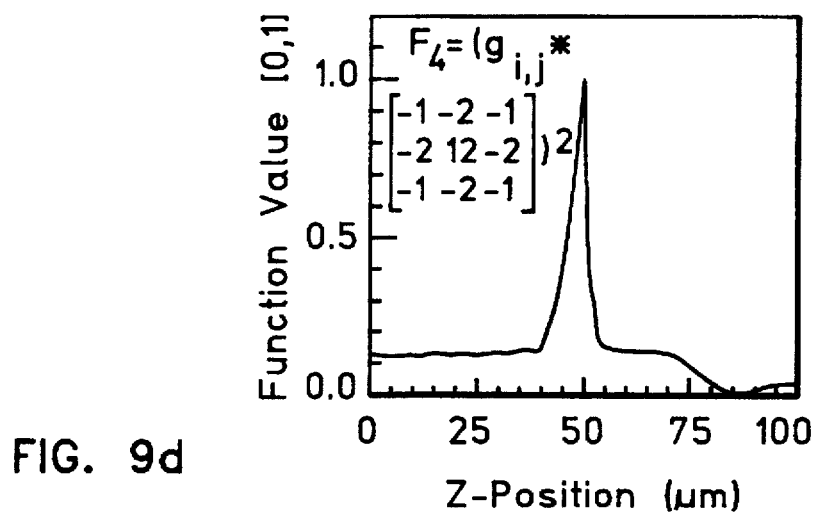
Figure 9E:
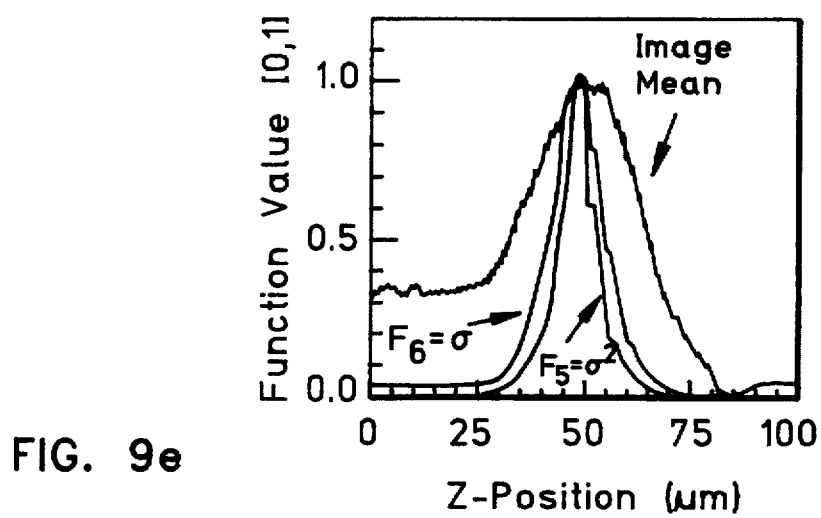
Figure 9F:
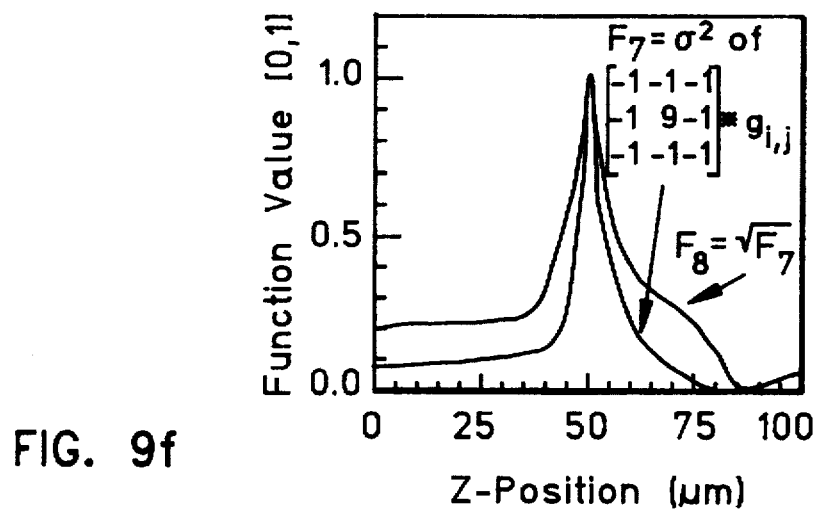
Figure 9G:
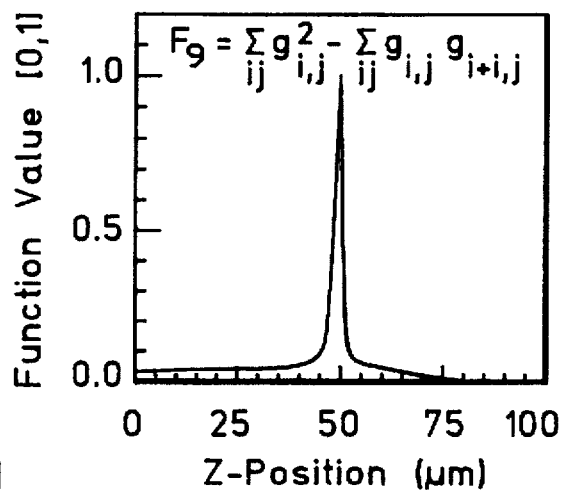
Figure 9H:
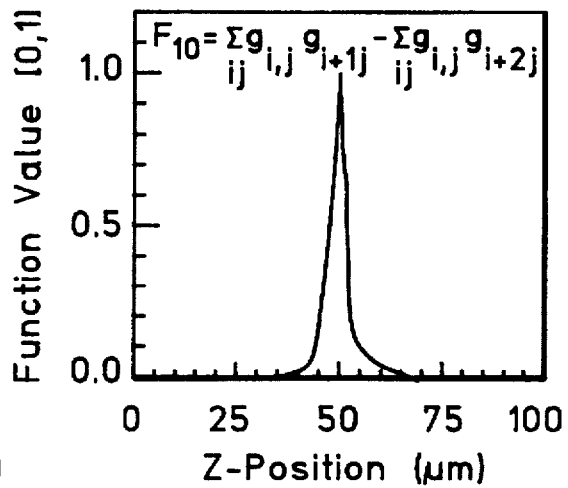
Figure 9I:
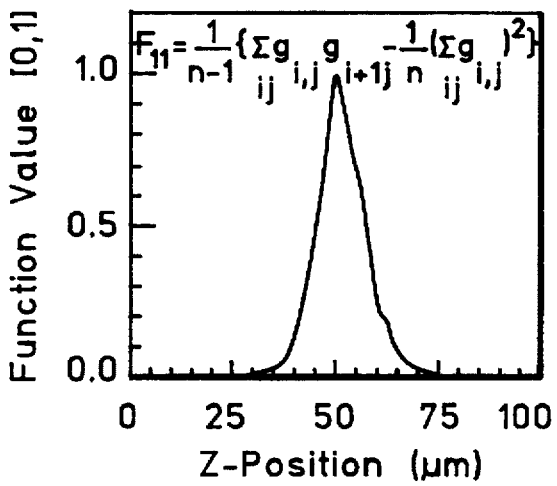
Figure 10A:
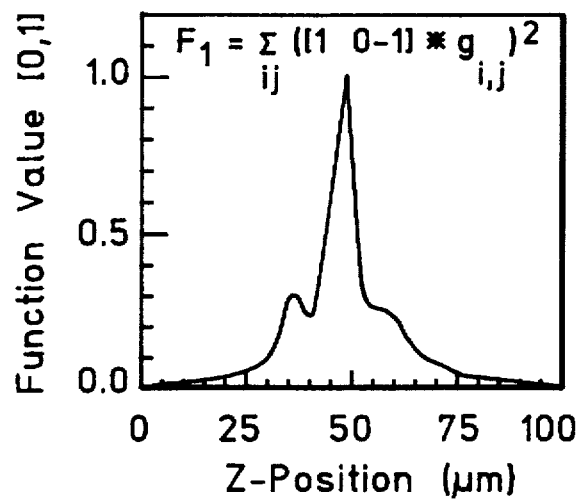
FIGS. 10a, 10b, 10c, 10d, 10e, 10f, 10g, 10h, and 10i illustrate autofocus function ($F_1$–$F_{11}$) results for a phase contrast microscope field containing a single cell using the system shown in FIG. 1.
Figure 10B:
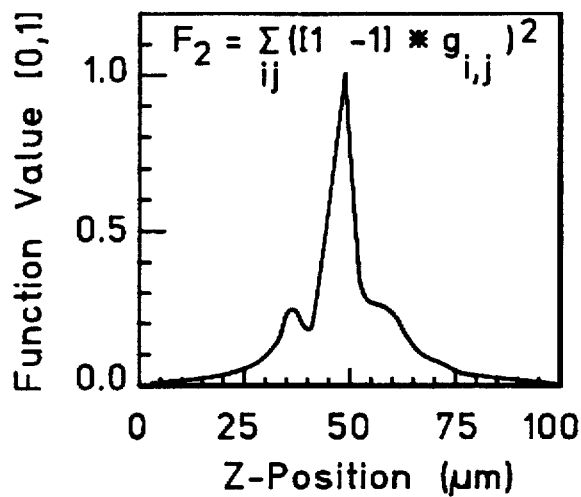
Figure 10C:
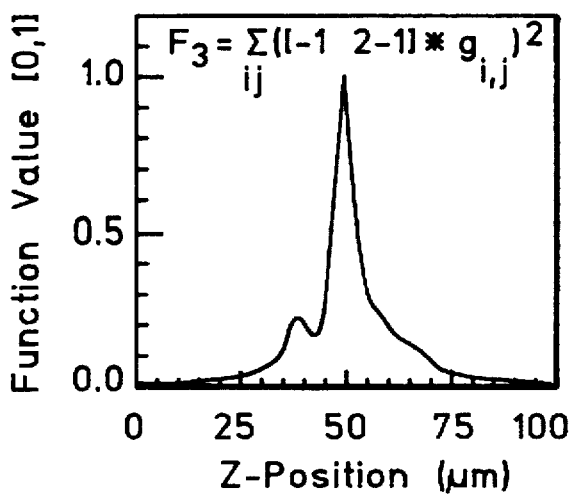
Figure 10D:
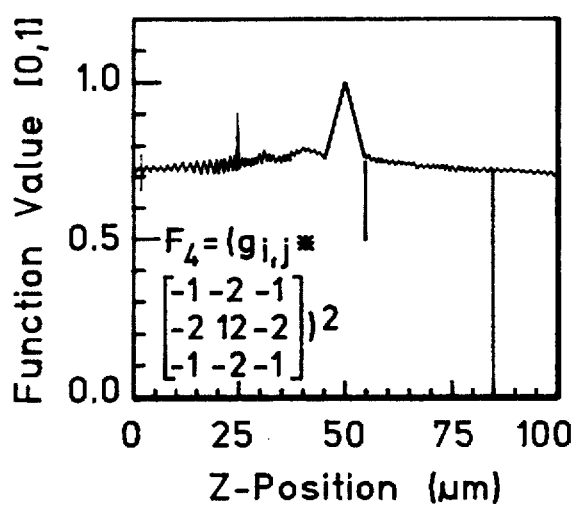
Figure 10E:
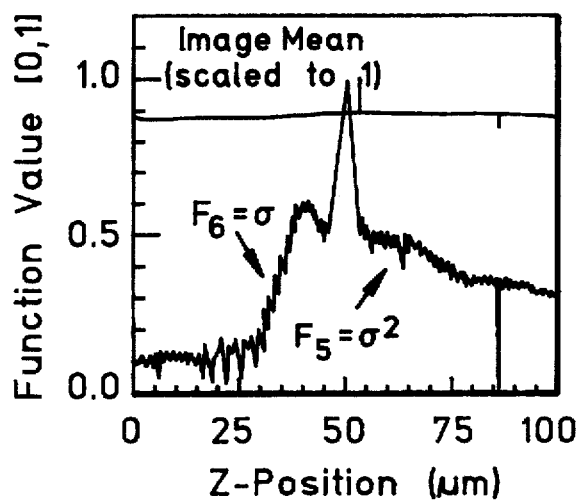
Figure 10F:
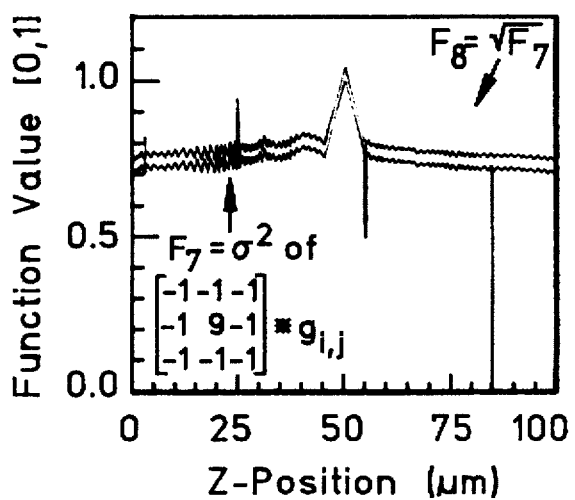
Figure 10G:
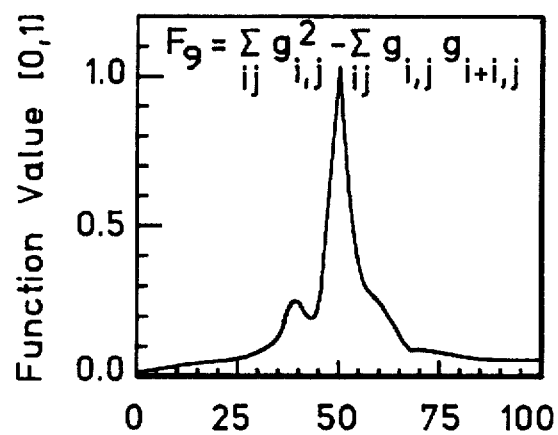
Figure 10H:
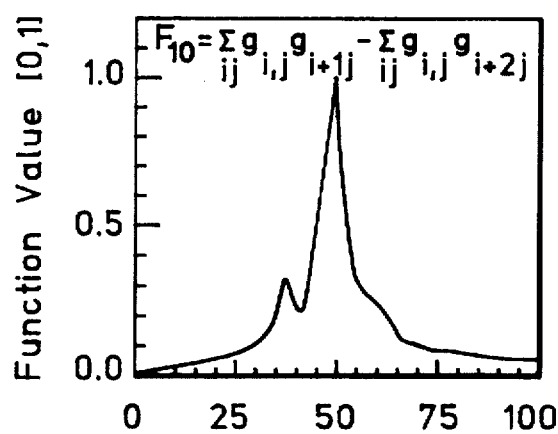
Figure 10I:
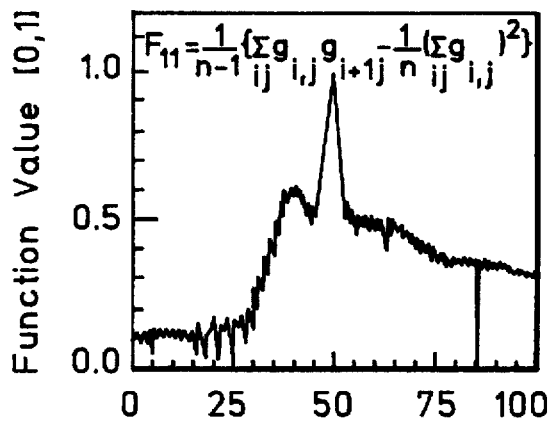

The autofocus functions were first tested on a microscope field containing ten cells. The focus was changed in 0.098 μm increments (4 out of 4096 digital steps in a 100 μm range), and at each position the functions were evaluated for both phase contrast and fluorescence before moving to the next position. FIG. 7 shows the plots of scaled function value versus position for fluorescence. While there are clear variations in peak widths and sharpness, the functions are primarily unimodal. Only functions dependent on statistical measures (FIGS. 7e, 7f and 7i) show side peaks, and those are probably not significant enough to cause an algorithm to focus incorrectly. These small side peaks also appear in the mean intensity (FIG. 7e). The repeating pattern of these peaks indicates that they are probably due to interference, rather than lamp fluctuations.

Table 2 summarizes the peak widths and best focus of each function for fluorescence. The widths at 90% of maximum show a clear dependence on the frequency characteristics of the function. Functions $F_1$, $F_2$ and $F_3$ are ordered from lowest to highest frequency enhancement and the peak widths narrow with higher frequency, giving $F_3$ the narrowest peak. $F_9$, which looks similar to $F_2$ in spatial filter terms, also has very similar 50% and 90% widths. The resolution functions have very narrow peaks, whereas the contrast functions have much wider peaks. The combination functions, $F_7$ and $F_8$, offer a trade off, with narrower peaks than the contrast functions and wider ranges than the resolution functions. The maxima, or best foci, for the predominantly statistical functions, $F_5$, $F_6$ and $F_{11}$ differ by 1.07 μm from the others. Although one field is inadequate to determine the significance of this difference, it raises the possibility that measures of contrast and resolution might not give the same focus.

TABLE 2

Autofocus Performance: Fluorescence, 10 Cells

| Function | Widths (μm) at Percent of Peak 50% | Widths (μm) at Percent of Peak 90% | Ratio 50%/90% | Best Focus |
|---|---|---|---|---|
| F1 | 5.20 | 1.85 | 2.8 | 48.742 |
| F2 | 4.95 | 1.70 | 2.9 | 48.742 |
| F3 | 3.33 | 1.13 | 2.9 | 48.742 |
| F4 | 4.95 | 1.65 | 3.0 | 48.742 |
| F5 | 9.86 | 2.96 | 3.3 | 47.668 |
| F6 | 16.20 | 4.20 | 3.8 | 47.668 |
| F7 | 6.10 | 2.45 | 2.5 | 48.742 |
| F8 | 11.00 | 3.35 | 3.3 | 48.742 |
| F9 | 5.00 | 1.70 | 2.9 | 48.742 |
| F10 | 5.28 | 2.00 | 2.6 | 48.742 |
| F11 | 9.90 | 2.95 | 3.4 | 47.668 |

The phase contrast results from the same experiment on a field with ten cells are shown in FIG. 8 and Table 3. In FIG. 8 it is immediately obvious that the peaks are not as sharp and that the plots are more irregular. There is a tendency toward side peaks in all the plots and these are especially prominent in FIGS. 8e and 8i with the statistical functions. It can also be seen that the tendency toward side peaks is reduced by higher frequency response filters, with progressive reduction in the first shoulder from $F_1$ through $F_2$ and $F_3$ in FIGS. 8a, 8b, and 8c. The same trends as with fluorescence are visible in the peak widths. That is, the highest frequency response filters, $F_3$ and $F_4$, also have the narrowest peaks and the contrast functions have very wide ranges.

TABLE 3

Autofocus Performance: Phase Contrast, 10 Cells

| Function | Widths (μm) at Percent of Peak 50% | Widths (μm) at Percent of Peak 90% | Ratio 50%/90% | Best Focus |
|---|---|---|---|---|
| F1 | 5.73 | 1.95 | 2.9 | 49.621 |
| F2 | 5.55 | 1.92 | 2.9 | 49.621 |
| F3 | 5.35 | 1.88 | 2.8 | 49.621 |
| F4 | 5.34 | 1.80 | 3.0 | 50.012 |
| F5 | 22.05 | 2.55 | 8.6 | 49.915 |
| F6 | 37.95 | 3.35 | 11.3 | 49.915 |
| F7 | 5.54 | 1.90 | 2.9 | 50.012 |
| F8 | 8.00 | 2.20 | 3.6 | 50.012 |
| F9 | 5.55 | 1.95 | 2.8 | 49.621 |
| F10 | 5.77 | 2.09 | 2.8 | 49.621 |
| F11 | 26.25 | 3.20 | 8.2 | 49.915 |

2. Microscope Field with One Cell

The next experiment was performed in the same way on a microscope field containing a single cell. From the fluorescence data shown in FIG. 9 and Table 4, it can be seen that the peaks are narrower. This is probably caused by the reduced distribution of cellular components in the vertical direction. With more cells, it is more likely that portions will extend farther from the coverslip. This may be even more true with a nuclear stain as used here, since the nucleus usually causes a spherically shaped cellular bulge and is not directly adherent to the glass as is the cell membrane. When the depth of field is comparable to cell thickness, the width of the focus function will certainly depend on specimen thickness. Furthermore, functions $F_2$ and $F_3$ show 90% peak widths of only 0.12 μm in Table 4. This is considerably less than the theoretical depth of field of 0.74 μm. It may be because each result is a sum of a large number of pixels that is then squared. Summing a large number of pixels (245, 760) increases the signal-to-noise ratio significantly. Squaring narrows the peaks further. The depth of field derivation by Born and Wolf, loc. cit., p. 441, assumes a 20% loss in vertical resolution at the extremes of the focal section as measured by attenuation of the central image patch. Evidently the signal-to-noise characteristics of this implementation allow significantly better discrimination than a 20% change.

TABLE 4

Autofocus Performance: Fluorescence, Single Cell

| Function | Widths (μm) at Percent of Peak | | Ratio | Best |
|---|---|---|---|---|
| | 50% | 90% | 50%/90% | Focus |
| F1 | 2.95 | 1.06 | 2.8 | 49.719 |
| F2 | 2.10 | 0.12 | 17.5 | 49.817 |
| F3 | 1.65 | 0.12 | 13.7 | 49.817 |
| F4 | 4.28 | 1.01 | 4.2 | 49.719 |
| F5 | 13.68 | 3.15 | 4.3 | 49.426 |
| F6 | 17.85 | 5.10 | 3.5 | 49.426 |
| F7 | 5.81 | 1.16 | 5.0 | 49.426 |
| F8 | 12.78 | 1.76 | 7.3 | 49.426 |
| F9 | 2.13 | 0.30 | 7.1 | 49.817 |
| F10 | 3.45 | 0.40 | 8.6 | 49.719 |
| F11 | 13.00 | 3.55 | 3.7 | 49.231 |

From Table 4, there were again differences between maxima, or best foci, with the largest between the statistical functions and highpass filters. These differences, however, are less than with the data from the field with ten cells, raising the possibility that specimen thickness may have played a role.

The phase contrast data from the single cell experiment are shown in FIG. 10 and Table 5. From FIG. 10, it appears that phase contrast focus on a field with a single cell offered the most severe autofocus challenge. All the plots exhibit significant side peaks and some appear quite noisy ("noisy" here is descriptive only; it is probably not true that image noise caused this appearance). The statistical functions $F_5$, $F_6$ and $F_{11}$, in FIGS. 10e and 10i are both noisy and have the largest side peaks. $F_4$ in FIG. 10d also appears noisy. At first glance it was tempting to attribute the noisy appearance of $F_4$ to the frequency characteristics of the highpass filter. However, as noted before, the frequency response of a camera with rectangular pixels lowers the vertical frequencies, complicating attempts to explain the cause. $F_7$ and $F_8$ in FIG. 10f, mixtures of resolution and contrast functions, also appear noisy. The simple highpass filters $F_1$, $F_2$ and $F_3$ in FIGS. 10a, 10b, and 10c are smooth and exhibit the earlier observed decrease in side peaks with increasingly high frequency response. From Table 5, there are again some differences in best foci, but these differences are small.

TABLE 5

Autofocus Performance: Phase Contrast, Single Cell

| Function | Widths (μm) at Percent of Peak | | Ratio | Best |
|---|---|---|---|---|
| | 50% | 90% | 50%/90% | Focus |
| F1 | 4.85 | 1.42 | 3.4 | 51.282 |
| F2 | 4.12 | 1.23 | 3.3 | 51.282 |
| F3 | 3.40 | 1.03 | 3.3 | 51.282 |

TABLE 5-continued

Autofocus Performance: Phase Contrast, Single Cell

| Function | Widths (μm) at Percent of Peak | | Ratio | Best |
|---|---|---|---|---|
| | 50% | 90% | 50%/90% | Focus |
| F4† | — | — | — | 51.477 |
| F5 | 8.40 | 1.88 | 4.5 | 51.477 |
| F6 | 8.62 | 2.00 | 4.3 | 51.477 |
| F7† | — | — | — | 51.477 |
| F8† | — | — | — | 51.477 |
| F9 | 4.53 | 1.21 | 3.7 | 51.282 |
| F10 | 5.30 | 0.62 | 8.5 | 51.282 |
| F11 | 11.82 | 2.30 | 5.2 | 51.477 |

†Widths could not be determined due to multimodality (see FIG. 4)

Some indications of the sensitivity of the functions to lamp fluctuations in phase contrast can be seen in FIGS. 8 and 10. In both of the corresponding experiments, there were intensity spikes. In FIG. 8e, there is a mean intensity spike at the position of about 87 μm, and in FIG. 10e, one at near 55 μm and another at 85 μm. The mean intensity spike in FIG. 8e showed up in $F_4$, $F_7$ and $F_8$ in FIGS. 8d and 8f and slightly in $F_5$, $F_6$ and $F_{11}$ in FIGS. 8e and 8i. The resolution functions $F_1$–$F_3$ in FIGS. 8a–8c and the autocorrelation functions $F_9$ and $F_{10}$ in FIGS. 8g and 8h appear to have been immune from this lamp fluctuation. This same pattern is exhibited in FIG. 10. It is interesting to note that, with the exception of $F_5$, the functions that were sensitive to these lamp fluctuations are dependent on the contrast measures of variance or standard deviation.

3. Function Dependence on Magnification and Sampling

The data for phase contrast focus on a single cell suggested that the frequency response of the focus function plays an important role in the formation of side peaks. It is likely that these side peaks arise from interference just above and just below best focus. Interference would be expected occur at lower frequencies since the departure from best focus degrades the modulation transfer function (MTF) of the microscope creating a lower frequency cut off. If a focus function measured only the highest frequencies it should be immune from these effects. The focus function, however, is only one source of the frequency response. The microscope and the camera also have characteristic frequency responses that act prior to the focus function. Ideally, the camera should sample with at least twice the maximum frequency of the optical signal, according to the Nyquist sampling criterion. The Rayleigh resolution estimate, has been explained by others, such as Inoué (Inoué S, Video Microscopy, Plenum Press, New York, 1986) is $$d = \frac{1.22\lambda}{NA_{obj} + NA_{cond}} \tag{2}$$

where λ is the wavelength of light and NA is the numerical aperture. With a 0.52 NA condenser, a 0.75 NA objective, and a peak wavelength of 540 nm corresponding to the peak transmittance of the daylight filter utilized, the resolution was 0.518 μm. Thus, the image should have been magnified so that the distance between components of the specimen projected onto adjacent pixels corresponded to about 0.25 μm in the specimen. At a zoom of 1.0 with these optics, the projected distance was 0.607 μm. This represents a condition of undersampling and causes aliasing. Achieving Nyquist sampling would have required a zoom of 0.607/0.250=2.43, above the maximum available zoom of 2.25.

Unfortunately, the limited brightness in fluorescence microscopy can make Nyquist sampling highly impractical and even impossible. Intensity is proportional to the inverse square of the magnification and even with the bright preparation used here, a zoom of 2.25 forces operation of the camera and image processor at the upper limits of gain, resulting in a very noisy signal. Limited fluorescence intensity motivates the use of high NA, low magnification objectives that increase the problem of undersampling. Because of the signal loss with increased magnification, it is impractical to optimally sample for autofocus in fluorescence and undersampling conditions were maintained for these experiments.

Figure 11:
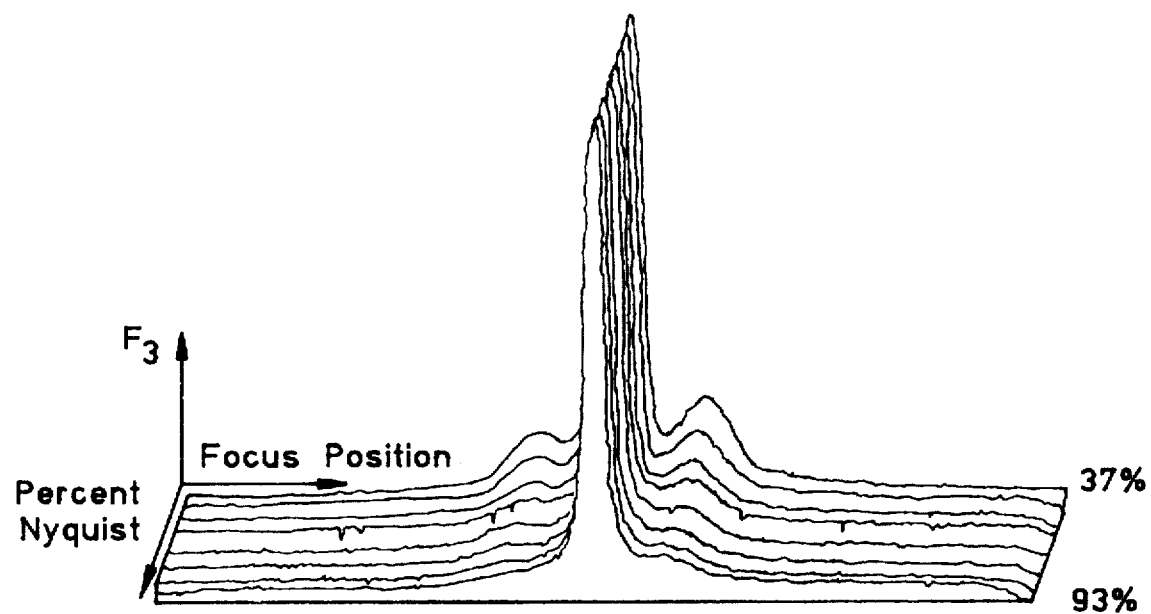
FIG. 11 is a three-dimensional plot of the response of function $F_3$ against focus position and zoom using the system shown in FIG. 1.

It is important, however, to understand the effects of sampling on autofocus, since many objectives and microscopes with different magnifications and NA's are available. To further study the dependence of the side peaks on magnification, an experiment on a microscope field with a single cell was carried out at a series of zooms, 0.9–2.25, that correspond to a range of 37–93% undersampling. A 3D plot of the response of function $F_3$ versus focus position and zoom is shown in FIG. 11. At a zoom of 0.9 the side peaks are big enough to cause an autofocus algorithm to locate a spurious best focus under some conditions. As predicted, increasing the magnification to nearly optimal sampling at 2.25 caused the side peaks to disappear. This experiment underscores the fact that the choice of optics and camera can be very important in determining focus function characteristics: anything that changes the resolution or the magnification will cause similar changes.

It was also observed, for example, that growing the cells on the coverslip instead of the slide increased the size of the side peaks (data not shown). This was due to the gain in resolution from placing the cells at the location where objective aberrations are best corrected as described by others, such as Gibson (Gibson S F F, Modeling the 3-D Imaging Properties of the Fluorescence Light Microscope, Ph. D. Dissertation, Carnegie Mellon University, Pittsburgh, Pa., 1990). The index of refraction of the mounting media, thickness of the coverslip, dirt in the optical path, illumination wavelength, and camera and image processor electronics are other components that can alter the system MTF, such as described by Inoué, and change the shape of the focus function.

B. Autofocus Performance in Automated Scanning

Finally, phase contrast and fluorescence autofocus were tested in a series of experiments scanning rectangular areas of >1000 fields. The purpose of these experiments was to test the hypothesis that the weighted average is a good estimate of best focus, measure autofocus precision, determine how small a number of focus positions could be used without compromising precision in an attempt to achieve maximum speed, and compare the best focus between phase contrast and fluorescence.

Several rectangular areas on different specimens were scanned in a raster pattern, with refocusing performed 20 times in fluorescence and then 20 times in phase contrast. $F_3$ was used in phase contrast for all experiments and either $F_3$ or a variation of $F_7$, where the filter was [−1 2.5 −1], were used for fluorescence. These choices were based on consideration of peak sharpness and unimodality. With scanning microscopy, a operation over a large vertical range is not as important because the best foci of adjacent fields are usually not far apart. In addition, those functions resulting in the largest range also had problems with unimodality on a single cell in phase contrast. Therefore, the highest frequency response filter was chosen for phase contrast. For fluorescence, $F_3$ gave a narrow enough range with a single cell (1.03 µm 50% peak width from Table 5) to be a problem even for scanning microscopy. Therefore, $F_7$ and $F_3$ were considered good candidates. Since the real-time implementation utilized the interlaced camera signal, the variation of $F_7$ substituting a 1D sharpening filter for the 2D filter was used.

1. Accuracy, Precision and Speed

For each set of 20 autofocus tests, mean and standard deviation were calculated for both the maximum and the weighted average of best focus. The differences between the means of the maxima and weighted averages were also calculated to determine if the weighted average was a comparatively accurate estimate of best focus.

The results of these tests are shown in FIG. 12. From the combined standard deviations, the autofocus precision in phase contrast averaged 0.154 µm with the maximum and 0.069 µm with the weighted average. In fluorescence the precision averaged 0.230 µm for the maximum and 0.159 µm for the weighted average. This is considerably better than the 0.74 µm depth of field of the 20×, 0.75 NA objective. In all but the first experiment the precision was better with phase contrast than with fluorescence. There are a number of factors that could have contributed to this difference. In phase contrast, the image was strobed near the end of the video field after the piezoelectric focus had stopped at its new position, whereas in fluorescence, each field was integrating on the CCD while focus was changing (30–50% of the field duration). Also, as previously discussed, the cellular and nuclear components may have been distributed differently.

The statistics from the difference of the maxima and weighted averages showed a very good agreement between the two estimates of best focus. In phase contrast, the differences ranged from −0.025 to 0.014 µm and the largest standard deviation was 0.071 µm. In fluorescence, the differences ranged from −0.002 to 0.044 with a maximum standard deviation of 0.088 µm. Given this agreement between the two estimates and the improvement in combined standard deviation, it is clear that the weighted average was a better measure of best focus.

The above performance was obtained with focus times as short as 0.25 second (s) in phase contrast. There appeared to be no degradation in focus precision at 0.25 s with 11 focus positions tested. Therefore, even faster autofocus may be possible.

2. Phase Contrast Focus as an Estimate of Fluorescence Focus

The differences between the means of each set of focus tests in phase and fluorescence are shown in Table 6. Excluding experiment 2, where the fluorescence autofocus lost track for part of the scan, the average of the differences between the two microscope modes varied between −0.394 and 0.745 µm, with good agreement between the maxima and weighted averages. There are many possible causes of this difference in foci, including microscope alignment, focus sampling interval and differences between nuclear and cytoplasmic component distributions. These results indicate that measuring and correcting for the difference between the two microscope modes may yield significant improvement. It did not seem possible, however, to predict the difference from one specimen to another. Again excluding experiment 2, the average standard deviation was 0.347 µm for the maximum and 0.342 for the weighted average. Thus the standard deviation of the difference was about ½ the depth of field of the objective. Although this might be enough to cause a small loss of precision in fluorescent measurements, it indicates that phase contrast autofocus provided a good estimate of fluorescence autofocus.

TABLE 6

Comparison of Best Focus between
Phase and Fluorescence in Automated Scanning

| | Mean Phase-Mean Fluorescence | | | |
|---|---|---|---|---|
| | Maximum | | Weighted Average | |
| Experiment | Mean | s | Mean | s |
| 1 | 0.292 | 0.420 | 0.293 | 0.410 |
| 2* | 0.934 | 1.150 | 0.985 | 1.140 |
| 3 | 0.719 | 0.235 | 0.745 | 0.219 |
| 4 | −0.183 | 0.142 | −0.196 | 0.137 |
| 5 | −0.394 | 0.457 | −0.349 | 0.465 |
| 6 | −0.214 | 0.397 | −0.175 | 0.400 |
| 7 | −0.301 | 0.433 | −0.304 | 0.423 |

All measurements in microns.
*Fluorescence autofocus lost track for a portion of the scan.

IV. CONCLUSIONS

The experiments carried out with the presently preferred embodiment of the autofocus system of the present invention showed that it is possible to scan large areas of a microscope slide using phase contrast autofocus to minimize exposure for fluorescence imaging. This should make possible the imaging of living cells with minimal toxicity and the analysis of sensitive fluorescence preparations without photobleaching while focusing. There was a significant difference between best focus in phase contrast and fluorescence, but the difference was constant enough to allow correction. In addition, it was shown that autofocus can be performed with precision an order of magnitude better than the depth of field in less than 0.25 s. Improved precision was achieved using the weighted average, which made use of the data from all focus positions tested.

The power-weighted average is the average of the positions, each weighted by a power of the focus value at that position. The weighted average is calculated from the array of focus function results. Each focus function result is a magnitude resulting from calculation of the function over the entire image frame (245,760 pixels) or field (122,880 pixels) at a single position. The maximum does not account for the magnitude of the values at adjacent positions, while the weighted average does by averaging the function values at all positions.

This performance was achieved after minimizing the effects of undersampling by choosing autofocus functions with is the most prominent highpass filter characteristics. The problem of undersampling could be even more severe with lower magnification, high NA objectives and higher NA condensers. Multimodality was even more severe for functions less dependent on resolution and particularly severe with contrast measures. The lack of unimodality with intensity variance (or standard deviation) in phase contrast autofocus makes use of contrast-based functions more questionable. The interference postulated to cause this problem may be present with all forms of transmitted microscopy where the image elements are small in number or regularly spaced.

For fluorescence, the fact that brightness is also directly dependent on distance from best focus may overwhelm the unwanted interference contrast extrema. All autofocus functions tested here decrease in magnitude with decreasing image intensity. The attenuated fluorescence may decrease or eliminate multimodality in the contrast measures of focus. The highpass filter functions have an even narrower range because of this intensity dependence. By combining the statistical and resolution measures, the range can be broadened while retaining a relatively narrow peak. Such a combination may be important for scanning sparsely populated cell specimens and necessary for autofocus applications requiring greater operating range.

The level of autofocus reliability and speed achieved here is an important step in bringing measurements common in flow cytometry closer to practical use in scanning cytometry. Such measurements may have advantages related to in situ analyses, such as morphology, relationship and position not possible with flow cytometry. Position may be a particular advantage for time lapse analysis of living cells where cell-by-cell tracking would be possible with short scan intervals.

While the above detailed description has shown, described, and pointed out the fundamental novel features of the invention as applied to various embodiments, it will be understood that various omissions and substitutions and changes in the form and details of the device illustrated may be made by those skilled in the art, without departing from the spirit of the invention.

What is claimed is:

1. A sequential method of autofocus for a microscope having a focus mechanism, the method comprising:

scanning a specimen on a microscope stage;

sequentially receiving digital images of the specimen at a plurality of vertical positions along a Z axis;

for each vertical position of the plurality of vertical positions:

applying a digital filter to a digital image acquired at the vertical position to obtain a filtered image; and applying a measurement function to the filtered image to obtain a value representing a degree of focus;

applying a weight to the value representing a degree of focus to obtain a weighted value;

applying a non-interative function to a plurality of weighted values of focus to obtain a focus position; and causing the microscope stage to move to a vertical position corresponding to the focus position.

2. The method of claim 1, wherein the non-interative function is a weight-averaged function and the focus position is a weight-averaged position.

3. The method of claim 2, wherein the weight-averaged function corresponds to:

$$W_a = \frac{\sum_z z F_z^n}{\sum_z F_z^n}$$

Where:

Wa is the weight averaged position;

z is a vertical position of the plurality of vertical positions;

$F_z$ is a value representing a degree of focus at the vertical position; and n is a weighing power.

4. The method of claim 3, where the plurality of vertical positions constitutes a search range.

5. The method of claim 4, where the search range has increments corresponding with the plurality of vertical positions in which each increment is smaller than a depth of field of the microscope.

6. The method of claim 5, where applying a non-iterative function is performed a first time with n set to a first weighing power value to obtain a first weight averaged position and then a second time with n set to a second weighing power value to obtain a second weight-averaged position and the weight-averaged position is obtained by taking either the first weight averaged position or the second weight-averaged position.

7. The method of claim 2, wherein the digital filter performs a sharpening transformation.

8. The method of claim 2, wherein the measurement function measures contrast.

9. The method of claim 2, wherein the measurement function measures resolution.

10. The method of claim 1, wherein the non-iterative function is a curve-fitting function.

11. The method of claim 10, wherein the digital filter performs a sharpening function.

12. The method of claim 10, wherein the measurement function measures contrast.

13. The method of claim 10, wherein the measurement function measures resolution.

14. In an autofocus apparatus for a microscope having a focus method, an improvement comprising:

means for scanning a specimen on a microscope stage;

means for acquiring a digital image of the specimen at a plurality of vertical positions along a Z axis;

means for applying a digital filter to a digital image acquired at each vertical position of the plurality of vertical positions to obtain a filtered image;

means for applying a measurement function and a weight to a filtered image to sequentially obtain a plurality of weighted values, each weighted value representing a degree of focus;

means for applying a non-iterative function to the plurality of weighted values to obtain a focus position; and means for causing the microscope stage to move to a vertical position corresponding to the focus position.

15. The improvement of claim 14, wherein the non-iterative function is a weight-averaged function.

16. The improvement of claim 15, wherein the weight averaged function is:

$$W_a = \frac{\sum_z z F_z^n}{\sum_z F_z^n}$$

Where:

Wa is the weight averaged position;

z is a vertical position of the plurality of vertical positions;

$F_z$ is a value representing a degree of focus at the vertical position; and n is a weighing power.

17. The improvement of claim 16, wherein the plurality of vertical positions constitutes a search range.

18. The improvement of claim 17, where the search range has increments corresponding with the plurality of vertical positions in which each increment is smaller than a depth of field of the microscope.

19. The improvement of claim 18, where the means for applying the non-iterative function first obtains a first weight-averaged position with n set to a first weighing power value and then obtains a second weight-averaged position with n set to a second weighing power value and the focus position is obtained by taking either the first weight averaged position or the second weight averaged position.

20. The improvement of claim 14, where the non-iterative function is a curve-fitting function.

* * * * *